(12) United States Patent
Thompson

(10) Patent No.: US 6,571,125 B2
(45) Date of Patent: May 27, 2003

(54) DRUG DELIVERY DEVICE

(75) Inventor: David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/781,750

(22) Filed: Feb. 12, 2001

(65) Prior Publication Data

US 2002/0111601 A1 Aug. 15, 2002

(51) Int. Cl.[7] ............................................. A61M 5/00
(52) U.S. Cl. ........................ 604/20; 604/891.1; 128/260
(58) Field of Search ............................. 604/891.1, 20; 128/260

(56) References Cited

U.S. PATENT DOCUMENTS 4,140,121 A * 2/1979 Kuhl et al. .................. 128/260
4,793,825 A * 12/1988 Benjamin et al. ......... 604/891.1

(List continued on next page.)

OTHER PUBLICATIONS

Bae et al., "Pulsatile Drug Release by Electric Stimulus," ACS Symposium Series, Ch. 8, 545, p. 98–110 (1994).
Kwon et al., "Electrically Erodible Polymer Gel for Controlled Release of Drugs," Nature, vol. 354, p. 291–294 (1991).

(List continued on next page.)

*Primary Examiner*—Philippe Derakshani
(74) *Attorney, Agent, or Firm*—Girma Wolde-Michael; Michael C. Soldner

(57) ABSTRACT

An Implantable Medical Device (IMD) for controllably releasing a biologically-active agent such as a drug to a body is disclosed. The IMD includes a catheter having one or more ports, each of which is individually controlled by a respective pair of conductive members located in proximity to the port. According to the invention, a voltage potential difference generated across a respective pair of conductive members is used to control drug delivery via the respective port. In one embodiment of the current invention, each port includes a cap member formed of a conductive material. This cap member is electrically coupled to one of the conductive members associated with the port to form an anode. The second one of the conductive members is located in proximity to the port and serves as a cathode. When the cap member is exposed to a conductive fluid such as blood, a potential difference generated between the conductors causes current to flow from the anode to the catheter, dissolving the cap so that a biologically active agent is released to the body. In another embodiment of the invention, each port is in proximity to a reservoir or other expandable member containing a cross-linked polymer gel of the type that expands when placed within an electrical field. Creation of an electric field between respective conductive members across the cross-linked polymer gel causes the gel to expand. In one embodiment, this expansion causes the expandable member to assume a state that blocks the exit of the drug from the respective port. Alternatively, the expansion may be utilized to assert a force on a bolus of the drug so that it is delivered via the respective port. Drug delivery is controlled by a control circuit that selectively activates one or more of the predetermined ports.

20 Claims, 15 Drawing Sheets

U.S. PATENT DOCUMENTS

| | | | |
|---|---|---|---|
| 4,902,278 A | * 2/1990 | Maget et al. | 604/891.1 |
| 5,016,646 A | 5/1991 | Gotthardt et al. | 128/784 |
| 5,165,403 A | 11/1992 | Mehra | 128/419 D |
| 5,292,338 A | 3/1994 | Bardy | 607/5 |
| 5,305,745 A | 4/1994 | Zacouto | 128/637 |
| 5,306,293 A | 4/1994 | Zacouto | 607/17 |
| 5,314,430 A | 5/1994 | Bardy | 607/5 |
| 5,368,704 A | 11/1994 | Madou et al. | 204/129.55 |
| 5,551,849 A | 9/1996 | Christiansen | 417/472 |
| 5,609,622 A | 3/1997 | Soukup et al. | 607/122 |
| 5,651,979 A | 7/1997 | Ron et al. | 424/423 |
| 5,662,689 A | 9/1997 | Elsberry et al. | 607/5 |
| 5,700,481 A | * 12/1997 | Iga et al. | 604/20 |
| 5,797,898 A | 8/1998 | Santini, Jr. et al. | 604/890.1 |
| 5,817,131 A | 10/1998 | Elsberry et al. | 607/5 |
| 5,820,589 A | 10/1998 | Torgerson et al. | 604/93 |
| 5,845,396 A | 12/1998 | Altman et al. | 29/885 |
| 5,876,741 A | 3/1999 | Ron | 424/423 |
| 5,893,881 A | 4/1999 | Elsberry et al. | 607/5 |
| 5,935,159 A | 8/1999 | Cross, Jr. et al. | 607/116 |
| 5,968,087 A | 10/1999 | Hess et al. | 607/127 |
| 6,002,955 A | 12/1999 | Willems et al. | 600/374 |
| 6,178,349 B1 | 1/2001 | Kieval | 607/3 |

OTHER PUBLICATIONS

Li et al., "Reversal of Reflex–Induced Myocardial Ischemia by Median Nerve Stimulation: A Feline Model of Electroacupuncture," *Circulation*, 97(12), p. 1186–1194 (Mar. 31, 1998).

"Glue' for Biochips Developed," *Medical Device & Diagnostic Industry*, p. 20 (Nov. 2000).

"Smart' Implants Could Assist Patient Medication," *Medical Device & Diagnostic Industry*, p. 21–22 (Nov. 2000).

* cited by examiner

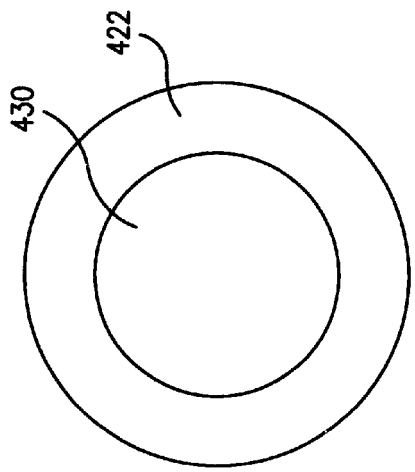
FIG. 14A
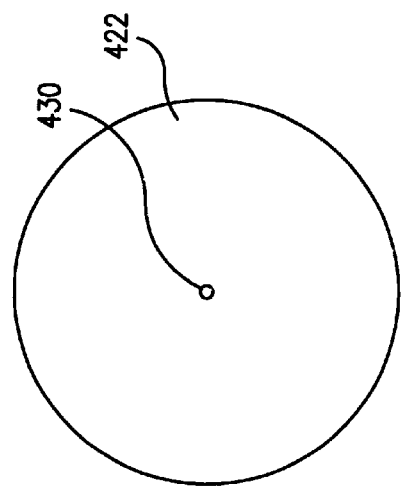
FIG. 14B
FIG. 14C
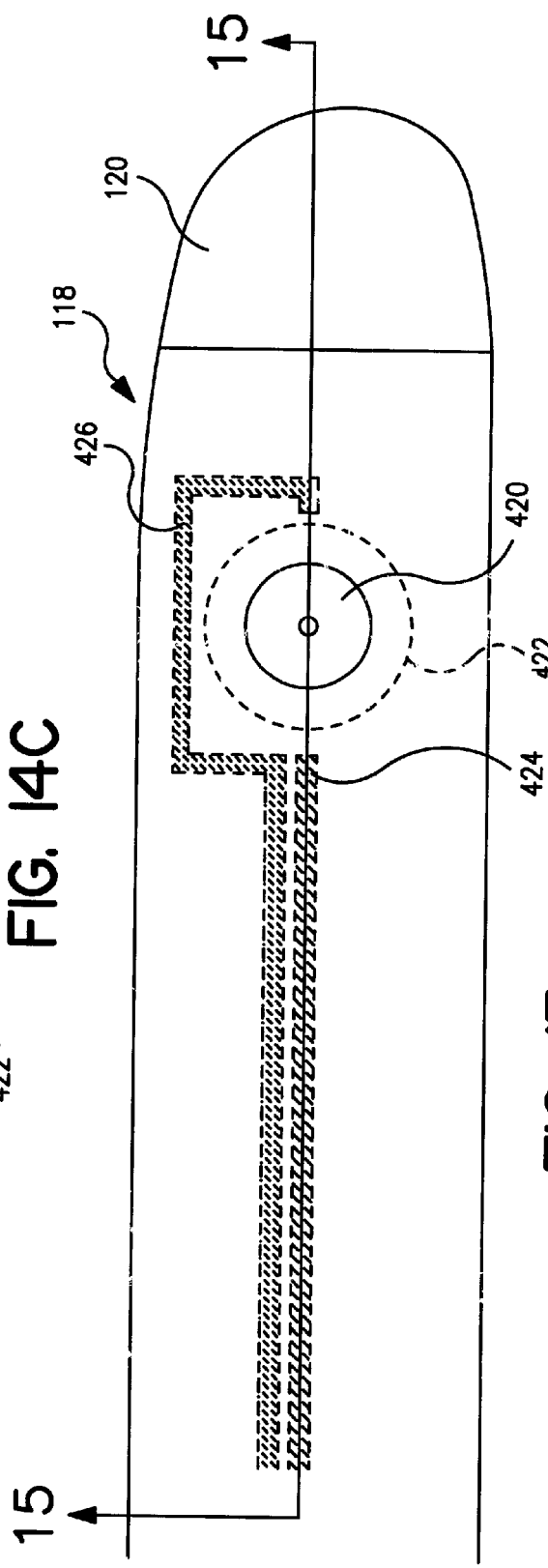
FIG. 13

DRUG DELIVERY DEVICE

FIELD OF THE INVENTION

The present invention concerns a system for treating a physiological disorder using a drug delivery catheter; and, more particularly, relates to an implantable medical device to remotely deliver drugs, and in some instances, electrical stimulation, to a patient to regulate the heart, the vascular system, and other bodily systems.

BACKGROUND OF THE INVENTION

Drug delivery therapies are often a primary component of an overall patient health plan. The successful use of many drugs is often dependent upon the manner in which the drugs are administered. Some therapies require that the drug be delivered in response to specific biofeedback indicators. Other treatments prescribe the use of predetermined drugs over a long period of time. This makes the selection of a proper drug delivery method problematic. Additionally, lack of patient compliance may render a drug therapy program ineffective. Drug delivery also becomes problematic when the drugs are too potent for systemic delivery.

For all of the foregoing reasons, it is often desirable to utilize an implantable drug delivery system. Implantable drug delivery systems are in widespread use to provide site-specific and/or sustained delivery of beneficial agents to address adverse patient conditions. Such delivery systems may include implantable infusion pumps, which typically include a pressurized drug reservoir and some form of fluid flow control.

While implantable drug delivery systems are known, such systems are generally not capable of accurately controlling the dosage of drugs delivered to the patient. This is particularly essential when dealing with drugs that can be toxic in higher concentrations. One manner of controlling drug delivery involves using electro-release techniques for controlling the delivery of a biologically-active agent or drug. The delivery process can be controlled by selectively activating the electro-release system, or by adjusting the rate of release. Several systems of this nature are described in U.S. Pat. Nos. 5,876,741 and 5,651,979 which describe a system for delivering active substances into an environment using polymer gel networks. Another drug delivery system is described in U.S. Pat. No. 5,797,898 to Santini, Jr. which discusses the use of switches provided on a microchip to control the delivery of drugs. Yet another delivery device is discussed in U.S. Pat. No. 5,368,704 which describes the use of an array of valves formed on a monolithic substrate that can be selectively activated to control the flow rate of a substance through the substrate.

None of the foregoing references describe a manner of utilizing an electro-release system within an implantable medical device such as a catheter. Therefore, what.is needed is an improved electro-release system for selectively delivering drugs alone, or in combination with, electrical stimulation to a patient to provide an optimal therapy that is not dependent on patient compliance.

SUMMARY OF THE INVENTION

The current invention provides an Implantable Medical Device (IMD) for controllably releasing a biologically-active agent such as a drug to a body. In one embodiment, the IMD includes a catheter having one or more ports, each of which is individually controlled by a respective pair of conductive members located in proximity to the port. According to the invention, a voltage potential difference generated across a respective pair of conductive members is used to control drug delivery via the respective port.

In one embodiment of the current invention, each port includes a cap member formed of a conductive material. This cap member is electrically coupled to one of the conductive members associated with the port to form an anode. The second one of the conductive members is located in proximity to the port and serves as a cathode. When the cap member is exposed to a conductive fluid such as blood, a potential difference may be generated to cause current flow from the anode to the catheter. This causes the cap member to oxidize and dissolve in the blood, which allows a biologically-active agent to be released from the catheter into the blood.

In another embodiment of the invention, each port is in proximity to a reservoir or other expandable member containing a cross-linked polymer gel of the type that expands when placed within an electrical field. Generation of a voltage potential difference in the respective conductive members associated with the port creates an electric field across the cross-linked polymer gel, causing it to expand. This expansion exerts a force on the walls of reservoir or expandable member containing the gel, which may, in turn, be used to control the release of the biologically-active agent. According to one embodiment, the expandable member is a disk having an aperture in the center that swells to a closed state upon generation of the electric field. When the aperture is in the closed state, the biologically-active agent is prevented from exiting the port. According to another embodiment, the swelling of the polymer gel exerts a force against a flexible member that forms at least a portion of the reservoir containing the polymer gel. As a result, the flexible member covers the catheter port, preventing delivery of the drug through the port. In an alternative configuration, force exerted by expansion of the polymer exerts force against a slidable member that forms at least one wall of the reservoir. As a result, slidable member exerts a force against a bolus of a drug that is located within a second reservoir of the catheter, forcing a dosage of the drug from the port.

The catheter of the current invention may include local reservoirs containing the biologically-active agents. These local reservoirs are located in proximity to a respective port. Each of the reservoirs may contain the same, or a different, biologically-active agent as compared to the other local reservoirs. Alternatively, a storage reservoir may be located remotely within an IMD coupled to the proximal end of the catheter. In this case, the remote storage reservoir may be coupled to a drug infusion pump that pumps the agent contained within the remote reservoir to one or more of the ports via-an internal lumen within the catheter body.

According to another aspect of the current invention, the IMD may include a control circuit to selectively activate one or more of the conductor pairs, thereby controlling the delivery of one or more drugs via the respective ports.

In one embodiment of the invention, the catheter may include one or more electrodes to provide electrical stimulation to the body. The control circuit of the IMD may include means to coordination this electrical stimulation with the drug delivery therapy. For example, an analgesic agent may be delivered to the body at a predetermined time prior to the delivery of cardioversion/defibrillation stimulation to thereby minimize patient discomfort associated with the electrical stimulation.

In another embodiment of the invention, the catheter may include one or more biological sensors to provide one or more biological signals to the control circuit of the IMD. The control circuit may include means to control the delivery of the electrical stimulation and/or drug delivery therapy based on the one or more biological signals provided by the biological sensors.

According to yet another aspect of the invention, the ports of the catheter may be of varying sizes. By selectively allowing drug delivery to be performed via a predetermined combination of these ports, a precise drug dosage may be released to the body.

Other aspects of the invention will be apparent to those skilled in the art from the following description and the accompanying drawings.

BRIEF DESCRIPTION OF THE DRAWINGS

FIG. 13 is a top view of another embodiment of a catheter that employs an expanded polymer gel to prevent the biologically-active agent from exiting a catheter port.

FIG. 14A is a top plan view of the disk member of the catheter of FIG. 13 when the gel is not in an expanded state.

FIG. 14B is a top plan view of the disk member of the catheter of FIG. 13 when the gel is in an expanded state.

FIG. 14C is a side plan view of the disk member of the catheter of FIG. 13.

DETAILED DESCRIPTION OF THE PREFERRED EMBODIMENTS

The present invention provides an Implantable Medical Device. (IMD) that is adapted to controllably deliver one or more biologically-active agents to a body from a local and/or remote source. In one embodiment, this IMD includes a catheter including, or coupled to, one or more reservoirs storing the one or more biologically-active agents. These agents are controllably released upon generation of control signals by the control circuitry of the IMD, as is discussed in detail below.

Figure 1:
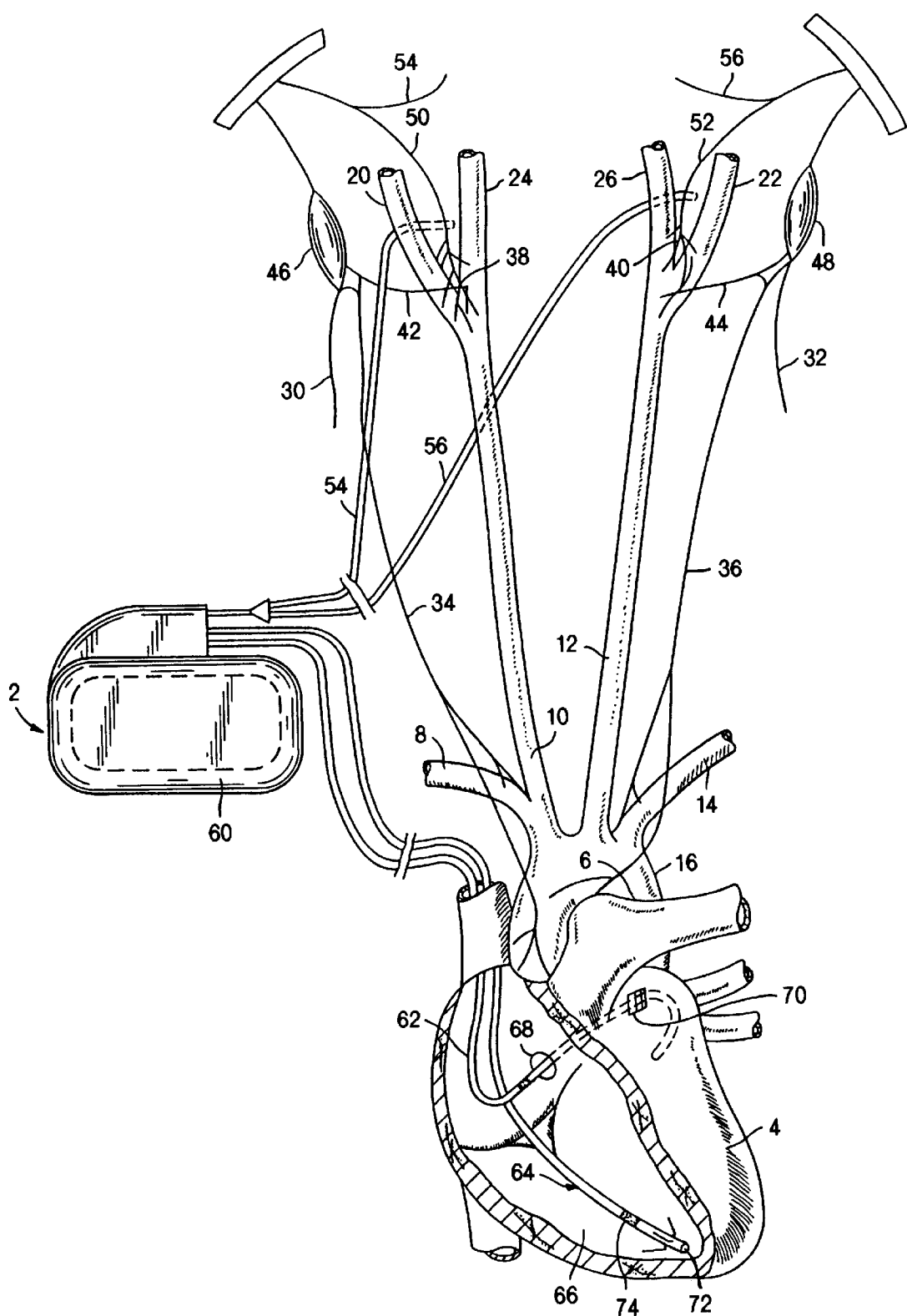
FIG. 1 is a plan view of an implantable medical device and drug delivery system according to one embodiment of the invention.

FIG. 1 is a plan view of an implantable medical device 2 and drug delivery system according to one embodiment of the invention. According to this embodiment, the inventive system is employed to deliver drugs to selected nerves to control a patient's heart rate. FIG. 1 includes an illustration of a patient's vascular system, diagramming heart 4 and the associated vascular and nervous system. The heart pumps oxygenated blood out through the aortic arch 6, which leads to a right subclavian artery 8, a right common carotid 10, a left common carotid 12, a left subclavian artery 14, and a thoracic aorta 16. The bifurcation of the carotid arteries 10 and 12 leads to external carotid arteries 20 and 22, respectively, and further to internal carotid arteries 24 and 26, respectively.

FIG. 1 further shows vagus nerves 30 and 32 that are intercoupled to the aortic arch 6 via cardiac depressor nerves 34 and 36, respectively. The areas immediately above the bifurcations of the carotid arteries 10 and 12 are referred to as the carotid sinus bodies 38 and 40. A number of nerves extend from the stretch receptors at the bifurcation of the carotid arteries in the carotid sinus. For example, nerve branches 42 and 44 extend from the carotid sinus bodies 38 and 40, respectively, and join the ganglions 46 and 48, respectively, of the vagus nerves. Other nerve fibers comprising the carotid sinus nerve branches 50 and 52 of the glossopharyngeal nerves 54 and 56, respectively, also extend from the carotid sinus bodies 38 and 40.

According to one use of the current inventive system, an implantable medical device (IMD) 2 is provided to control the remote delivery of biologically-active agents such as veratrum alkaloid to the vagus nerves. IMD 2 is shown coupled to two catheters 54 and 56, although only one, or more than two, catheters may be used. These catheters, which may be of any of the embodiments discussed below, are shown implanted in the proximity of the right and left carotid sinus nerves 50 and 52, respectively. The specific location of these catheters may be varied along the carotid sinus nerves, and it is contemplated that in the practice of the present invention it may be possible to place such stimulators in the vicinity of any of the nerves shown in FIG. 1, such as any of the nerves associated with the myocardial baroreceptors.

The IMD 2 includes internal circuitry and an electrically-activated power source for selectively controlling the delivery of one or more biologically-active agents via catheters 54 and 56 in a manner to be described below. The power source may assume a wide variety of forms, such as a battery, a large capacitor with a slow discharge rate, or various other mechanical devices. Further, as described elsewhere, the IMD 2 may include additional circuitry for sensing and interpreting cardiovascular activity, and for activating and deactivating electrodes provided on catheters 54 and 56 to provide electrical stimulation to predetermined nerves in conjunction with the delivery of biologically-active agents.

The exemplary use of the current invention in accordance with FIG. 1 provides a marked improvement over previous stimulation systems incorporating only an electrode. By controlling heart rate through the chemical and electrical stimulation of selected nerves, the required level and/or duration of electrode stimulation is greatly reduced, thereby improving battery life and avoiding nerve desensitization. Further, where the nerve stimulating drug is a veratrum alkaloid, direct application of the veratrum alkaloid to the selected nerve avoids the toxicity and side effects encountered with systemic delivery. Finally, by coordinating electrical stimulation as provided by the one or more electrodes provided by catheters 54 and 56 with the drug therapy, optimized treatment can be achieved. Various mechanisms for coordinating electrical stimulation and drug therapy are described in commonly-assigned U.S. Pat. No. 6,178,349 issued Jan. 23, 2001 entitled "Drug Delivery Neural Stimulation Device for Treatment of Cardiovascular Disorders" incorporated herein by reference in its entirety.

IMD 2 may further include a pulse generation circuit to deliver pacing or cardioversion stimulation pulses discussed further below. The pulse generation circuit may be of a type commonly known in the art and may include-an indifferent case electrode 60, and one or more electrodes positioned within the patient's vascular system. The embodiment of IMD 2 shown in FIG. 1 is coupled to two leads 62 and 64 implanted within a patient's right ventricle 66 and within the coronary sinus 68, respectively. Leads 62 and 64 may carry one or more sensors to provide an indication of performance of the heart 4, or any of the biological feedback indicators known in the art. For example, in one preferred embodiment, sensor 70 is carried on lead 62 to measure pH and/or blood oxygen levels.

Lead 64 is further shown carrying tip electrode 72 and ring electrode 74 to delivery pacing pulses and to sense electrical activity within the patient's heart. Alternatively, the electrode 72 may be positioned in the right atrium to sense atrial activity. This sensed electrical activity may be used by IMD 2 to determine the appropriate drug delivery therapy to be utilized according to the closed-loop mode of operation discussed below.

It will be appreciated that the afore-mentioned use of the current inventive system is by way of example only, and many therapies may be provided by the inventive drug delivery system. For example, IMD 2 may be useful as a response to ischemic conditions, such that the catheters 54 and 56 are placed about the median nerves. Cardiovascular regulation via median nerve stimulation is described, for example, in Li et al., "Reversal of Reflex-Induced Myocardial Ischemia by Median Nerve Stimulation: A Feline Model of Electroacupuncture," *Circulation* 97(12), pp. 1186–94 (Mar. 31, 1998), hereby incorporated by reference. Finally, while the device 2 is shown as preferably including two catheters 54 and 56, it is possible that only a single device need be provided.

Figure 2:
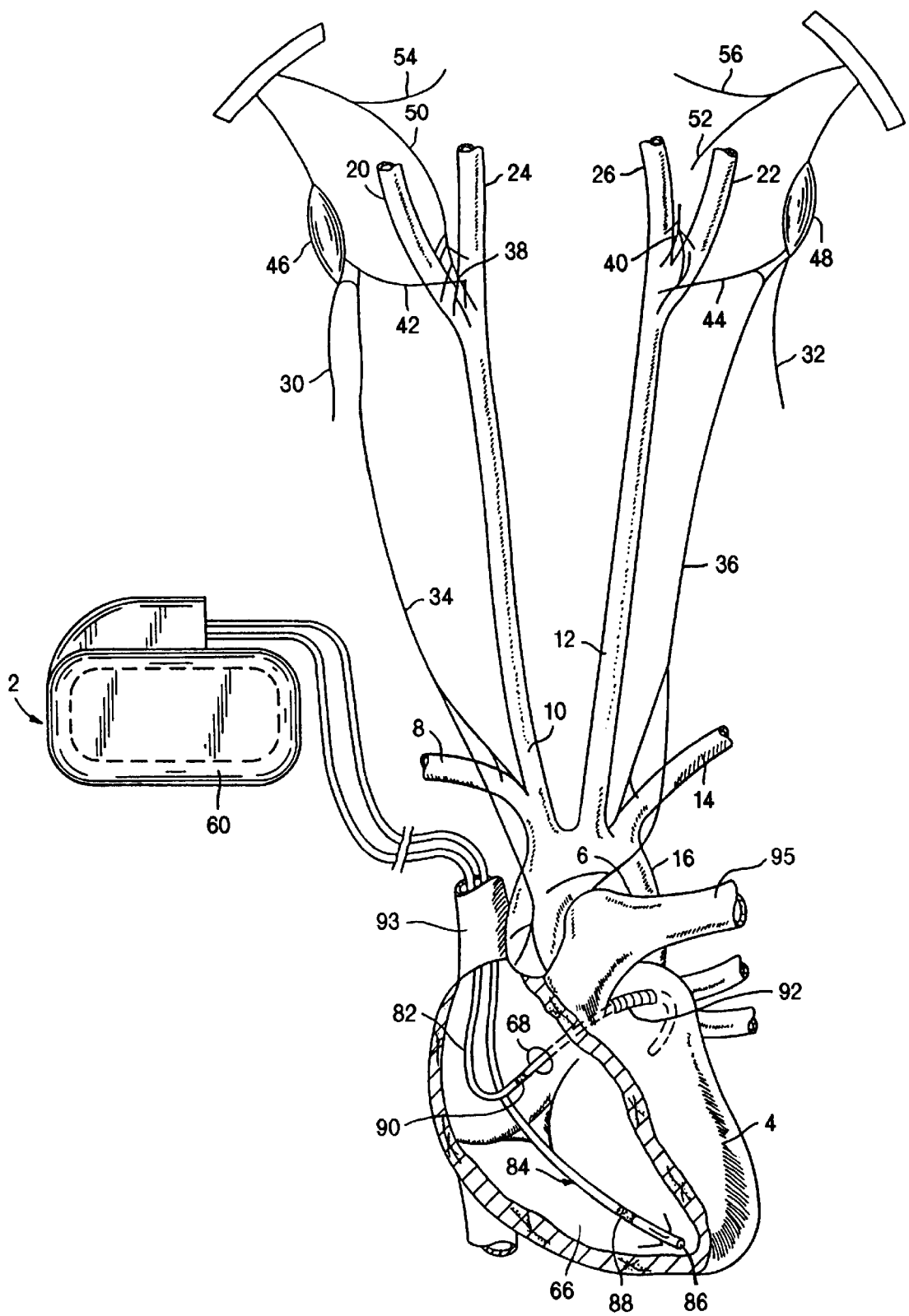
FIG. 2 illustrates an alternative embodiment of the present invention wherein drug delivery catheters are located within the heart or the associated vasculature.

FIG. 2 illustrates an alternative embodiment of the present invention wherein the drug delivery catheters are located within the heart or the associated vasculature. In this embodiment, IMD 2 is coupled to two catheters 82 and 84 that are drug delivery catheters for delivering biologically-active agents directly to the chambers of the heart. Catheters 82 and 84 further are shown to carry electrodes for providing electrical stimulation to the heart that may be performed alone, or in conjunction, with the drug delivery. For example catheter 82 includes tip and ring electrodes 86 and 88, respectively. In one embodiment, IMD 2 is capable of monitoring various physiological parameters using sensors carried on the body of catheters 82 and 84. For example, cardiac, blood or cardiovascular parameters may be monitored. Changes in $CO_2$ or oxygen levels, in pH, the concentration of lactice acid, alpha or beta myosin, catecholamines, endothelin, concentration of various ions such as potassium, calcium, or sodium ions, and/or certain coagulants or anti-coagulants are just some of the other parameters that may be monitored. In response to changes in these physiological parameters, various types of drug delivery therapy and/or electrical stimulation may be provided.

In one embodiment, therapy may include delivery of an agent for dissolving a forming blood clot. Such a device may prevent the establishment of a vascular haemorrhage or thrombosis by detecting blood coagulation and thereafter delivery thrombin inhibitors comprising small molecules such as, for example, D/N-methyl-phenylglycyl-Pro-arginal 0.5 mg/kg and/or hirudin 0.25 mg/kg, and/or aspirin 0.02 g or alternatively an inhibitor of factor XIII, such as a derivative of iodacetamide (for example fluoracetamide, 1 mg), or the delivery of a low dose of tPA. Such an inhibition of thrombin may control the tPA potential of the body so that the blood clot is dissolved. This type of therapy may be useful in preventing, or lessening the severity of, a stroke. Such therapies are discussed in U.S. Pat. Nos. 5,306,293 and 5,305,745 to Zacouto.

In another embodiment, one or more parameters indicative of cardiac failure may be monitored, with drug therapy being delivered based on a predetermined therapy schedule in response to the detected parameters. Other embodiments and/or uses for this type of system are discussed in the '293 and '745 patents to Zacouto referenced above.

Returning to FIG. 2, catheter 84 is shown to include a ring electrode 90 that may be used to provide electrical stimulation to the right atrium. Catheter 84 is further shown to include defibrillation coil electrode 92 positioned within the coronary sinus for delivering cardioversion and/or defibrillation stimulation to a patient. For example, a cardioversion shock may be delivered between coil electrode 92 and a second subcutaneous electrode (not shown) implanted below the skin of the patient's chest or back. Alternatively, one or more additional defibrillation electrodes may be carried on either of leads 82 and 84 and positioned within the superior vena cava 93, and/or the pulmonary artery 95,so that a cardioversion/defibrillation pulse may be applied between a predetermined pair of the defibrillation electrodes. Improved implantable atrial defibrillator and lead systems to terminate arrhythmias in this manner are described in commonly-assigned U.S. Pat. Nos. 5,165,403, 5,292,338, and 5,314,430 incorporated herein by reference in their entireties.

According to one embodiment of the invention, drug delivery may be coordinated with the delivery of cardioversion/defibrillation shocks to reduce, or eliminate, the pain associated with this therapy. For example, upon detection of atrial or ventricular fibrillation, IMD 2 may begin delivery of pain medication in preparation for delivery of the shock. The cardioversion shock is only delivered after sufficient time has elapsed to allow the medication to take effect. Systems of this nature are described in.commonly-assigned U.S. Pat. No. 5,817,131 to Elsberry entitled "Method and Apparatus for Alleviating Cardioversion Shock Pain", and in commonly-assigned U.S. Pat. Nos. 5,893,881 and 5,662,689 both entitled "Method and Apparatus for Alleviating Cardioversion Shock Pain by Delivering a Bolus of Analgesic", all of which are incorporated herein by reference in their entireties.

In yet another embodiment, drug delivery associated with the delivery of cardioversion/defibrillation shocks delivers biologically-active agents to reduce the defibrillation threshold, as discussed in the '131 patent referenced above. An agent such as D-salo-tol, Procainamide or Quinidine may be delivered as an alternative to, or in conjunction with, delivery of the pain alleviating therapies discussed above. The reduction of defibrillation threshold in such a case would provide the possibility of a reduced amplitude, less painful, cardioversion pulse. The delivery of a threshold reducing agent can therefore be employed as a pain alleviating therapy or as part of a pain alleviating therapy. In a more complex embodiment, two separate IMDs employing separate drug delivery devices might be employed to allow delivery of the threshold reducing agent alone or in conjunction with an analgesic. The threshold reducing agent may be delivered systemically, by means of catheters located in a peripheral blood vessel or the pericardial sac or may be retroperfused from the distal coronary sinus.

Figure 3:
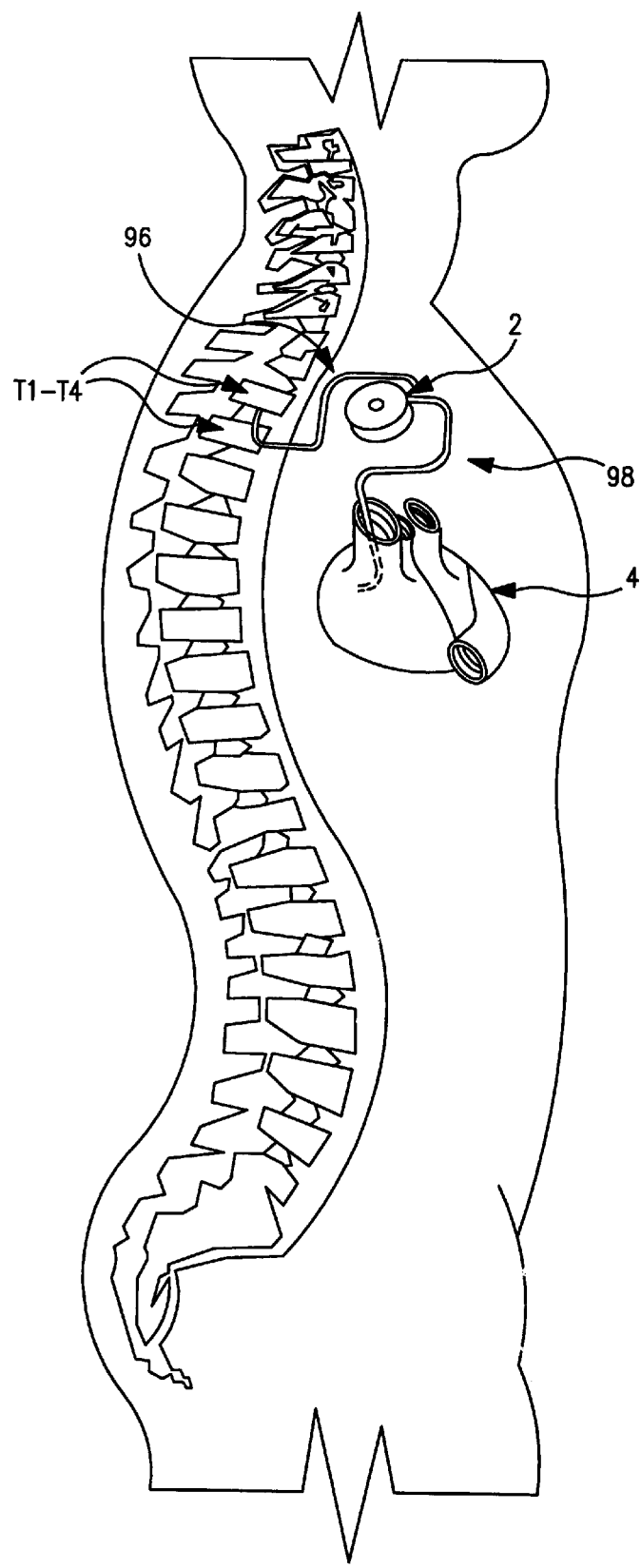
FIG. 3 illustrates the use of drug delivery catheters located near the region of the T1–T4 segments of the spine.

In one embodiment, drug delivery catheters used to reduce pain during cardioversion/defibrillation may be located in proximity to spinal nerves, as discussed further in conjunction with FIG. 3.

FIG. 3 illustrates the use of drug delivery catheters located near the region of the T1–T4 segments of the spine. The IMD 2 is capable of the sequential intrathecal delivery of a pain alleviating analgesic at therapeutic levels in the region of the T1–T4 segments of the spinal cord via one or more catheters 96. This drug therapy may be followed by delivery of atrial cardioversion electrical energy pulses or shocks of sufficient amplitude and duration to effectively cardiovert the heart 4 that has entered atrial fibrillation. This may be accomplished via one or more leads 98 carrying electrodes positioned in the chambers of the heart or associated vasculature. In another embodiment, the one or more catheters 96 may be used to deliver pain-relief drugs to this region of the body to alleviate pain that is not associated with a cardioversion shock, or to delivery drugs for reasons other than pain relief.

Figure 4:
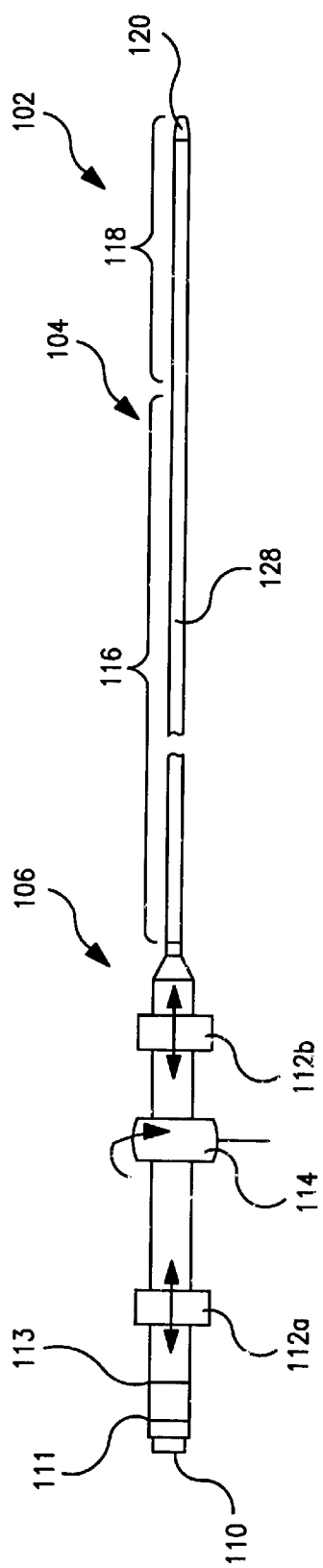
FIG. 4 is a plan view illustrating one embodiment of a drug delivery catheter assembly as may be used in accordance with the present invention.

FIG. 4 is a plan view illustrating one embodiment of a drug delivery catheter assembly 102 as may be used in accordance with the present invention. Catheter assembly 102 includes broadly a catheter 104 extending from a proximal assembly 106. Proximal assembly 106 includes a handle 108 to which an electrical connector 110 is mounted. One or more additional ring connectors may be provided on proximal assembly 106, such as ring connectors 111 and 113 discussed further below. Catheter may include longitudinally slidable manipulator wire control elements 112a and 112b and/or a rotatable core wire control element 114 that are movably mounted to handle 108 and that may be used to manipulate catheter 104 as described in commonly assigned U.S. Pat. No. 6,002,955.

Catheter 104 includes a main body portion 116, typically about 50 to 100 cm long, and a tip portion 118, typically about 5 to 25 cm long. While both main body portion 116 and tip portion 118 are flexible, tip portion 118 may be more flexible than main body portion 116. According to the invention, tip portion 118 includes a controllable drug eluting system to be described further below. Tip portion 118 may further include an electrode 120 which may be of any of the electrode configurations known in the art for providing electrical stimulation to body tissue. For example, electrode 120 may be a porous platinized electrode assembly. In one embodiment of the invention, additional electrodes such as ring electrodes may be provided by tip portion 118. In another embodiment, the catheter assembly need not provide any electrodes.

Figure 5:
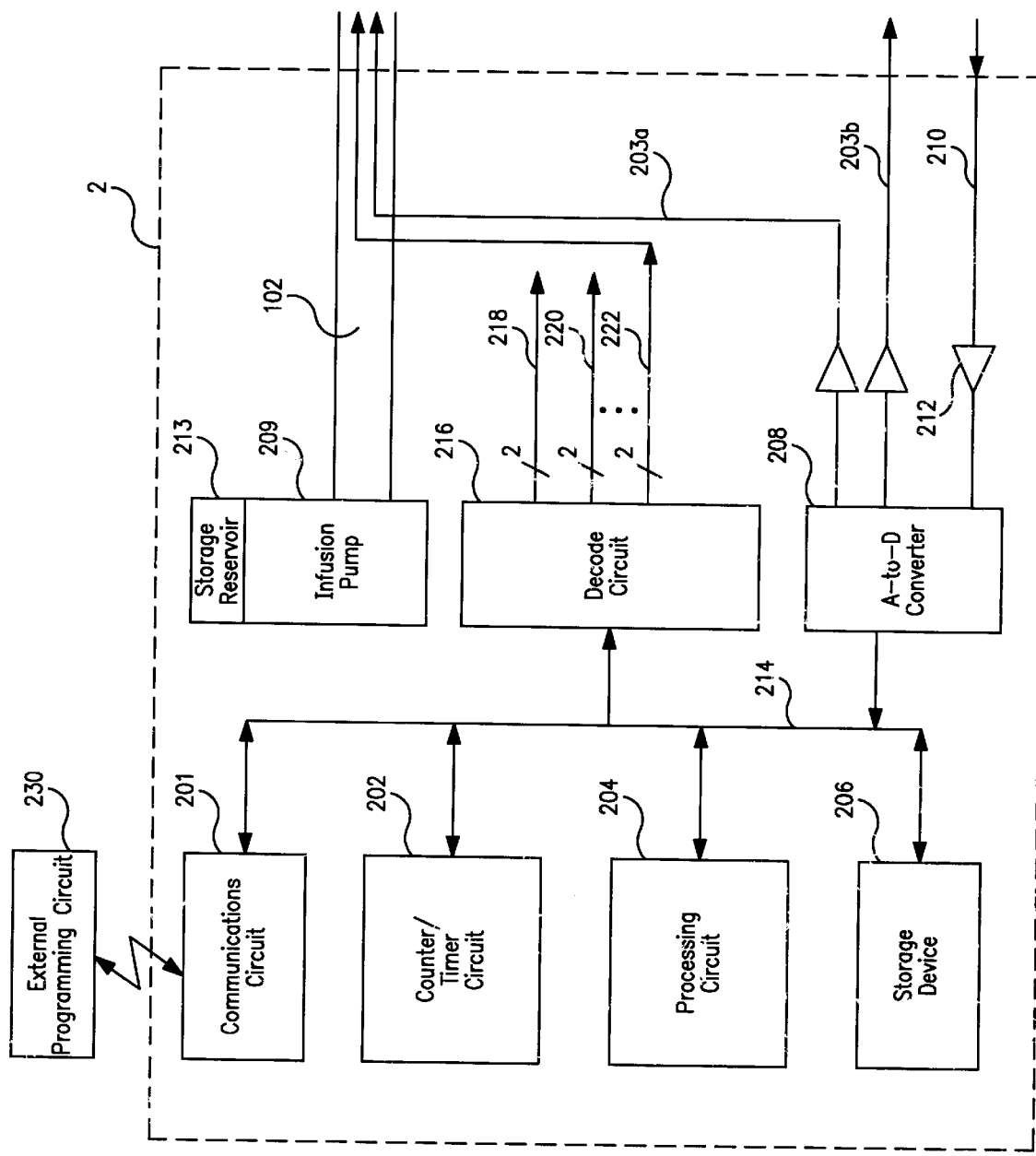
FIG. 5 is system block diagram of control circuitry that may be used in conjunction with a drug delivery system to deliver drug therapy and/or electrical stimulation to a patient.

FIG. 5 is system block diagram of a control circuit 200 that may be used to deliver drug therapy and/or electrical stimulation to a patient. Control circuit 200 may be included within any implantable medical device (IMD) known in the art, such as IMD 2 of FIG. 1. Control circuit 200 includes circuitry for delivering electrical stimulation for pacing, cardioversion, and/or defibrillation purposes on electrical stimulation outputs 203a and 203b. Control circuit may include a communications circuit 201 such as a telemetry system, counter/timer circuit 202, a processing circuit 204, and a storage device 206. Counter/timer circuit 202 may be utilized to generate the pacing and/or cardioversion/defibrillation pulses that are delivered via electrical stimulation outputs 203. Processing circuit 204 may be a microprocessor or other processing circuit as is known in the art. Storage device may comprise Random Access Memory (RAM), Read-Only Memory, registers, a combination thereof, or any other type of memory storage device suitable for use in implantable medical devices. Control circuit 200 may further include an Analog-to-Digital (A-to-D) converter 208, which receives input signals from one or more implantable sensors implanted at various locations within a body.

An IMD used in accordance with the current drug delivery system may also include a drug infusion pump such as pump 209 coupled to one or more drug delivery catheters such as catheter assembly 102. Pump 209 pumps a biologically-active agent stored within remote storage reservoir 213 through an inner lumen of catheter 102 in a manner prescribed by a predetermined drug therapy-regimen. Such a pump may be an implantable drug infusion pump with a programmable flow rate such as the SynchroMed pump commercially available from Medtronic Corporation. The SynchroMed is an internally powered programmable pump having features which allow physicians to change fluid delivery parameters, such as flow rate, infusion period, ramp time, and bolus volume. As an alternative, an implantable pump such as that described in commonly assigned U.S. Pat. No. 5,820,589, incorporated herein by reference, may be utilized. This alternative design provides a pump that is programmed noninvasively by means of a programmer that communicates flow rate information by means of radio frequency telemetry or other methods of non-invasive telemetry. The programmer also supplies power to the implantable pump during programming so that battery power is not required. An exemplary pump assembly is discussed further below with respect to various embodiments of the current drug delivery system.

In one embodiment, storage reservoir 213 coupled to the infusion pump may be refillable. For example, IMD 2 may include a port for receiving a syringe. The syringe may be inserted through subcutaneous tissue into the port to refill reservoir when the reservoir become partially or completely empty. An audible or other type of alarm may be provided to notify a patient when the reservoir has reached a predetermined fill level.

FIG. 5 further shows catheter 102 coupled to infusion pump 209. As illustrated in FIG. 4, catheter 102 may include one or more electrodes such as electrode 120. This electrode is coupled to electrical stimulation output 203a that is shown carried on the body of the catheter 102. Additional electrodes may be provided by catheter 102. The catheter may also carry one or more biological sensors as shown in FIG. 2. In this instance, one or more of the sensor inputs 210 are also coupled to conductors carried by the lead body.

In one embodiment of the invention, the drug delivery system operates in a closed-loop mode wherein one or more physiological signals that are received from one or more of the sensor inputs 210 triggers the delivery of biologically-active agents to a patient. In this mode, one or more physiological signal may be amplified by amplifier circuit 212, converted to digital format by A-to-D converter 208, and provided to processing circuit 204. Operating under software and/or hardware control, processing circuit analyzes the received signal(s) to determine a course of action. Based on this analysis, processing circuit may provide a predetermined address on bus 214 to decode circuit 216, which may be a demultiplexer. This, in turn, causes decode circuit 216 to drive one or more control signals shown as control lines 218, 220, and 222, which are normally in a high-impedance state. These control lines, which may extend to distal tip 118 of catheter 102, control the delivery of biologically-active agents according to the current invention. This will be discussed below in detail.

In the closed-loop system discussed above, many different biological signals may be monitored on sensor input(s) 210. For example, implanted sensors (not shown in FIG. 5) may monitor a patient's electrocardiam signals to detect a heart rate that is irregular, or that is too fast or too slow. Pressure, temperature, flow rate, motion, and/or activity sensors located within the heart or other areas of the body may monitor other physiological conditions. Still other sensors may be utilized to monitor a patient's blood chemistry to detect variations in hormone or other chemical levels, for example. This is discussed above in regards to the '293 and '745 patents to Zacouto. Processing circuit 204 may be programmed to respond to one or more trigger events sensed by the one or more sensors to active drug delivery and/or electrical stimulation in the manner discussed above.

In another embodiment of the invention, drug delivery may be performed in an open-loop manner that does not depend on bio-feedback. For example, counter/timer circuit 202 may be utilized to trigger drug delivery based on a programmed pre-selected time interval. Alternatively, an external programming circuit 230 may be used to initiate drug delivery via a communication with communication circuit 201 for example.

Drug Delivery Control Systems According to the Current Invention

As discussed above, the present invention provides an IMD that is adapted to controllably deliver biologically-active agents to a body. The IMD is coupled to a drug delivery catheter that may take the form of one of the embodiments discussed in the following paragraphs.

Figure 6:
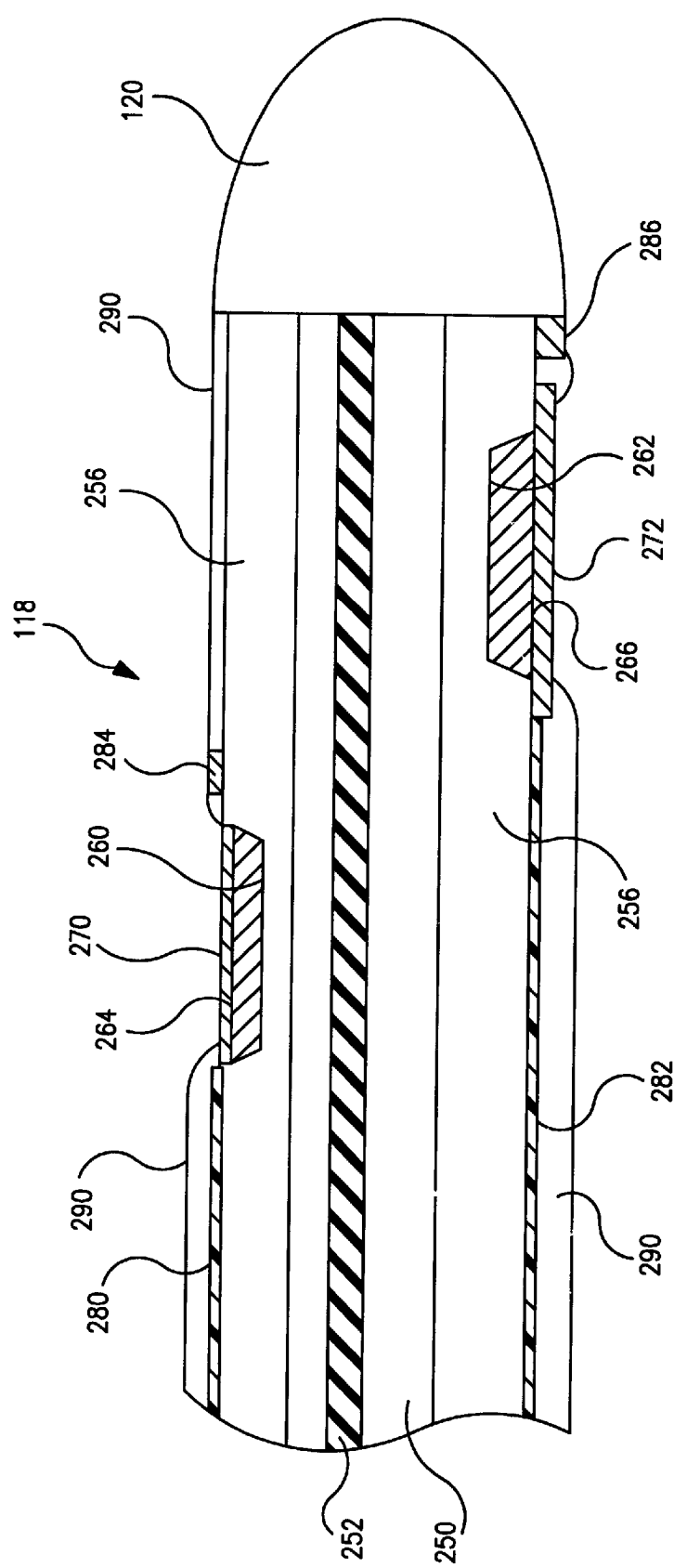
FIG. 6 is a side cutaway view of a catheter assembly having a conductive cap member covering a drug delivery port, wherein the cap member may be dissolved by passing an electrical current through the associated conductors.

FIG. 6 is a side cutaway view of tip portion 118 of catheter assembly 102 according to one embodiment of the current invention. In this embodiment, catheter assembly 102 includes a central lumen 250 that extends to electrode 120. Central lumen 250 carries a conductor 252 that couples electrode to connector 110 (FIG. 4). This conductor may be a coiled conductor, or a single or multi-filar stranded conductor of any of the configurations known in the art.

Central lumen 250 is defined by outer jacket 256 that may be formed of any biocompatible material that may be etched, such as polyethylene glycol or polytetrfluroethylene (PTFE) or a similar material. The outer jacket may be treated with a material to prevent tissue in-growth. For example, the outer jacket may be coated with a porous Polytetrafluoroethylene (PTFE) layer such as may be formed of expanded PTFE (e-PTFE) having a pore size of less than 10 microns or smaller. This is described in U.S. Pat. 5,609,622.

In this embodiment, etching of the jacket may be performed to create local reservoirs 260 and 262 which are each local to a respective drug delivery port. Although only two reservoirs are shown in the current example, any number of reservoirs may be provided on tip portion 118, and/or on body portion 116 of catheter assembly 102. Etching of the jacket may be accomplished using a chemical surface modification process, such as an etching process commercially performed by the Zeus Corporation, or, alternatively, by using a plasma or corona etching process. Reservoirs may be formed in any shape and depth that can be accommodated by the size of the tip portion 118 of catheter assembly.

Reservoirs 260 and 262 are filled with biologically-active compounds shown as compounds 264 and 266, respectively. Each of the reservoirs may be filled with the same, or a different, compound. Biologically-active compounds may include, but are not limited to, prodrugs, antisense, oligonucleotides, DNA, antibodies, vaccines, other recombinant proteins, anti-ADS substances, anti-cancer substances, antibiotics, immunosuppressants (e.g. cyclosporine) anti-viral substances, enzyme inhibitors, neurotoxins, opioids, hypnotics, antihistamines, lubricants tranquilizers, anti-convulsants, muscle relaxants and anti-Parkinson substances, anti-spasmodics and muscle contractants, miotics and anti-cholinergics, antiglaucoma compounds, anti-parasite and/or ant-iprotozoal compounds, anti-hypertensives, analgesics, anti-pyretics and anti-inflammatory agents such as NSAIDs, local anesthetics, ophthalmics, prostaglandins, anti-depressants, anti-psychotic substances; antiemetics, imaging agents, specific targeting agents, neurotransmitters, proteins, cell response modifiers, and vaccines. Other biologically-active compounds may include analgesics, anesthetics, spinal opiates, drugs adapted to increase the efficacy of defibrillation pulses or to reduce defibrillation thresholds such as D-solotal, Procainamide, or Quinidine, anti-seizure drugs, or any other biologically-active compound for which controlled, remote delivery may be applicable.

The biologically-active agents may be deposited within reservoirs using an injection process. The agents may be deposited in a pure form, such as a liquid solution or gel. Alternatively, these agents may be encapsulated within, or by, a release system. Use of a release system may be necessary to control the rate at which the biologically-active agents are released into the body. In this case, selection of the release system is dependent on the desired rate of release of the molecules. Both non-degradable and degradable release systems can be used for delivery of molecules. Suitable release systems include polymers and polymeric matrices, non-polymeric matrices, or inorganic and organic excipients and diluents such as, but not limited to, calcium carbonate and sugar. Release systems may be natural or synthetic, although synthetic release systems are preferred due to the better characterization of release profiles. The release system is selected based on the period over which release is desired, generally in the range of at least three to twelve months for in vivo applications. In contrast, release times as short as a few seconds may be desirable for some in vitro applications. In some cases, continuous (constant) release from a reservoir may be most useful. A further description of release systems is provided in U.S. Pat. No. 5,797,898 to Santini, Jr. et al entitled "Microchip Drug Delivery Devices", which is incorporated herein by reference in its entirety.

After the biologically-active agents are deposited within the reservoirs of the catheter assembly 102, reservoir cap members 270 and 272 are deposited over each of the reservoirs 260 and 262, respectively. Reservoir caps prevent the biologically-active agents from being released by the reservoirs until the selectable release is desired, as controlled by a control circuit to be discussed below. In one embodiment, each of the reservoir caps consists of thin films of conductive material sized to cover the respective reservoir, as shown by reservoir cap 270. In another embodiment, the thin film may extend beyond the edge of the reservoirs to partially cover the non-etched portion of jacket 256, as shown by reservoir cap 272. Any conductive material that can oxidize, is biocompatible and bio-absorbable, and that may be dissolved in solution such as blood upon application of an electric potential can be used for the fabrication of the anodes and cathodes. Examples of such materials include copper, gold, silver, and zinc, and some polymers, as described, for example, by I. C. Kwon et al., Electrically erodible polymer gel for controlled release of drugs", Nature, 1991, 354, 291–93; and Y. H. Bae et al., "Pulsatile drug release by electric stimulus", ACS Symposium Series, 1994, 545, 98–110.

Reservoir caps may be formed by injection or spin coating. Alternatively, each reservoir can be capped individually by capillary action, by drawing the material into the reservoir with a vacuum or other pressure gradient, by melting the material into the reservoir, by centrifugation and related processes, by inserting solids into the reservoir, or by any combination of these or similar methods.

Each of the reservoir caps is electrically and mechanically coupled to a respective conductor, which may be a wire. These conductors, which will be referred to as anode connectors for reasons to be discussed.below, are shown as conductors 280 and 282 of FIG. 6. These conductors 280 and 282 extend to the proximal assembly 106 to couple to a respective one of ring connectors 111 and 113 of FIG. 4. In one embodiment, each of the reservoir caps is coupled to a different one of the ring connectors. In an alternative embodiment, one or more reservoir caps may be electrically coupled to the same ring connector.

In addition to the conductors that are electrically coupled to the reservoir caps, additional "cathode" conductors are provided for each of the reservoirs. Each of these additional cathode conductors, shown in cross-section as conductors 284 and 286, are located adjacent to, but electrically and mechanically isolated from, a respective reservoir. The manner in which cathode conductors are routed is discussed below. Each of the cathode conductors is coupled to a respective connector on proximal assembly so as to form a complete circuit when a voltage difference is generated between the anode and the cathode conductors, and the cap member is placed in a conductive solution, as is discussed further below.

After conductors 280, 282, 284, and 286 are routed on an outer surface of jacket 256, an additional layer 290 of bio-compatible material may be provided.over a predetermined portion of jacket to cover portions of the conductors and hold them in place, but allowing the reservoir caps 270 and 272 and at least a portion of each cathode conductor to remain exposed. A layer of silicone may be extruded over parts of the main body portion 116 and tip portion 118, for example. Alternatively, an additional layer of PTFE may be deposited over jacket 256 and the conductors at selected locations.

As discussed above, each of the anode and cathode conductor pairs such as conductors 280 and 284 are adapted to form a circuit. This circuit is closed when the catheter is placed in a conductive solution such as blood or other bodily fluids. A voltage potential created between an anode conductor and a respective cathode conductor causes electrons to pass from the anode conductor to the cathode conductor through the conductive solution. This, in turn, causes the reservoir cap, which may be considered the anode of the circuit, to oxidize and dissolve into the surrounding fluids, exposing the biologically-reactive agent to surrounding body fluids for delivery.

The control of the conductor pairs via IMD 2 can be understood more clearly by returning to FIG. 5. Each of the conductor pairs 218, 220 and 222 of FIG. 5 are shown being carried by catheter 102, although it will be understood that some of the conductor pairs may be coupled to one or more additional catheters. Each of these conductor pairs corresponds with a respective reservoir in the manner discussed above. For example, conductor pair 218 of FIG. 5 may correspond to conductors 280 and 284, and reservoir 260 of FIG. 6. Fewer or more conductor pairs may be provided depending on the selected application. Processing circuit 204 provides a selected combination of signals on bus 214 to demultiplexer 216 to cause a voltage to be applied across a selected one of these conductor pairs. This results in a selected one of the reservoir caps being dissolved to release a desired biologically-active agent into the body. In one embodiment, processing circuit may cause decode circuit 216 to drive multiple conductor pairs in parallel or in sequence in response to sensor input so that multiple biological agents are released.

Figure 7:
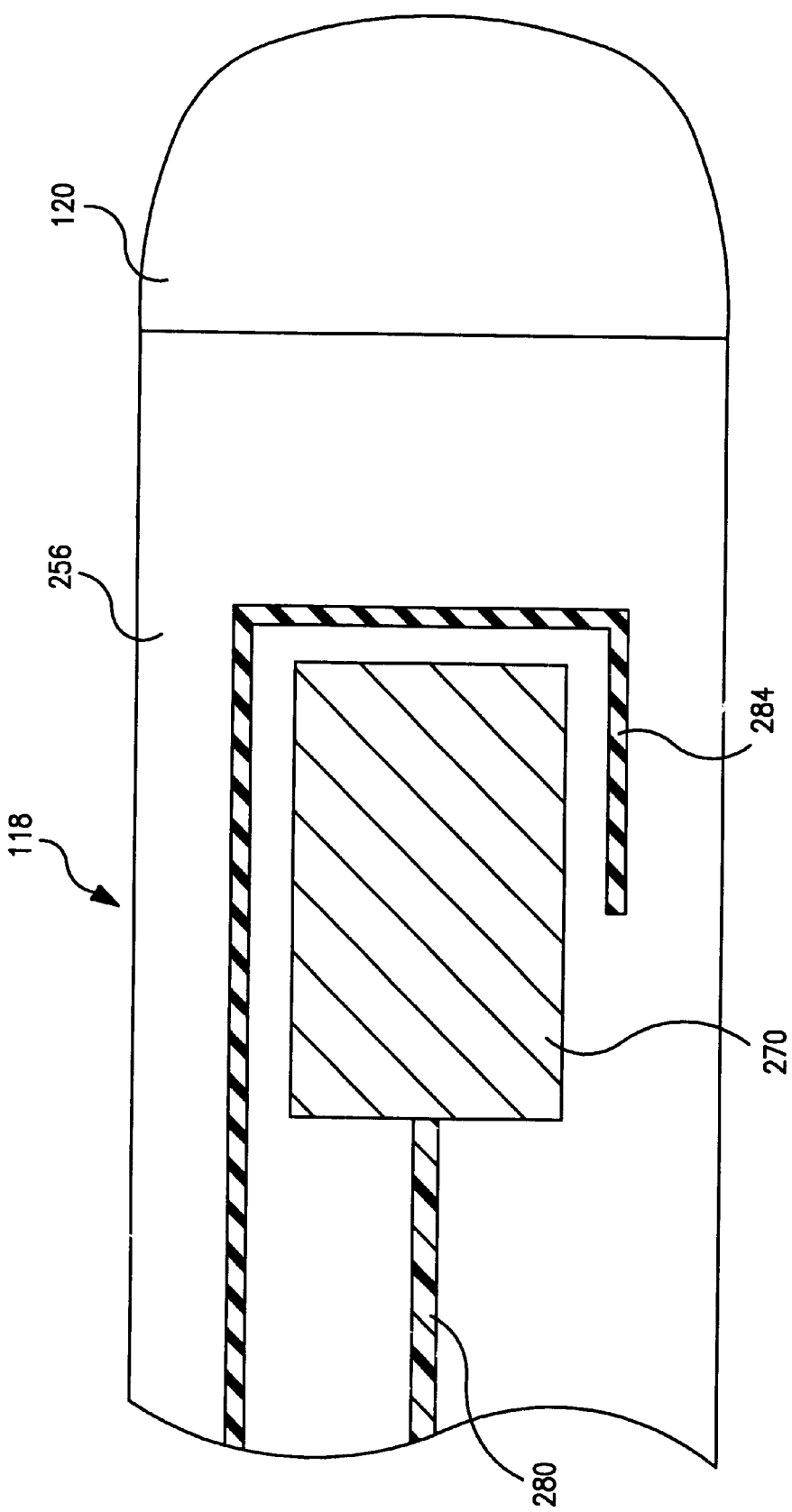
FIG. 7 is a top plan view of.the catheter of FIG. 6 before the outer layer of the jacket is formed on the catheter.

FIG. 7 is a top plan view of tip portion 118 of catheter assembly 102 illustrating reservoir cap 270 and the associated conductors before any additional layer 290 of biocompatible material is applied to the catheter assembly. This view shows the manner in which wire 284, which serves as the-cathode conductor, is adjacent to, but electrically isolated from, reservoir 270. Wire 280 is mechanically and electrically coupled to reservoir 270 in the manner discussed above.

The foregoing example discusses an embodiment wherein the anode and cathode conductors are provided external to jacket 256. In another embodiment, these conductors may be provided within inner lumens of the catheter assembly 102.

Figure 8:
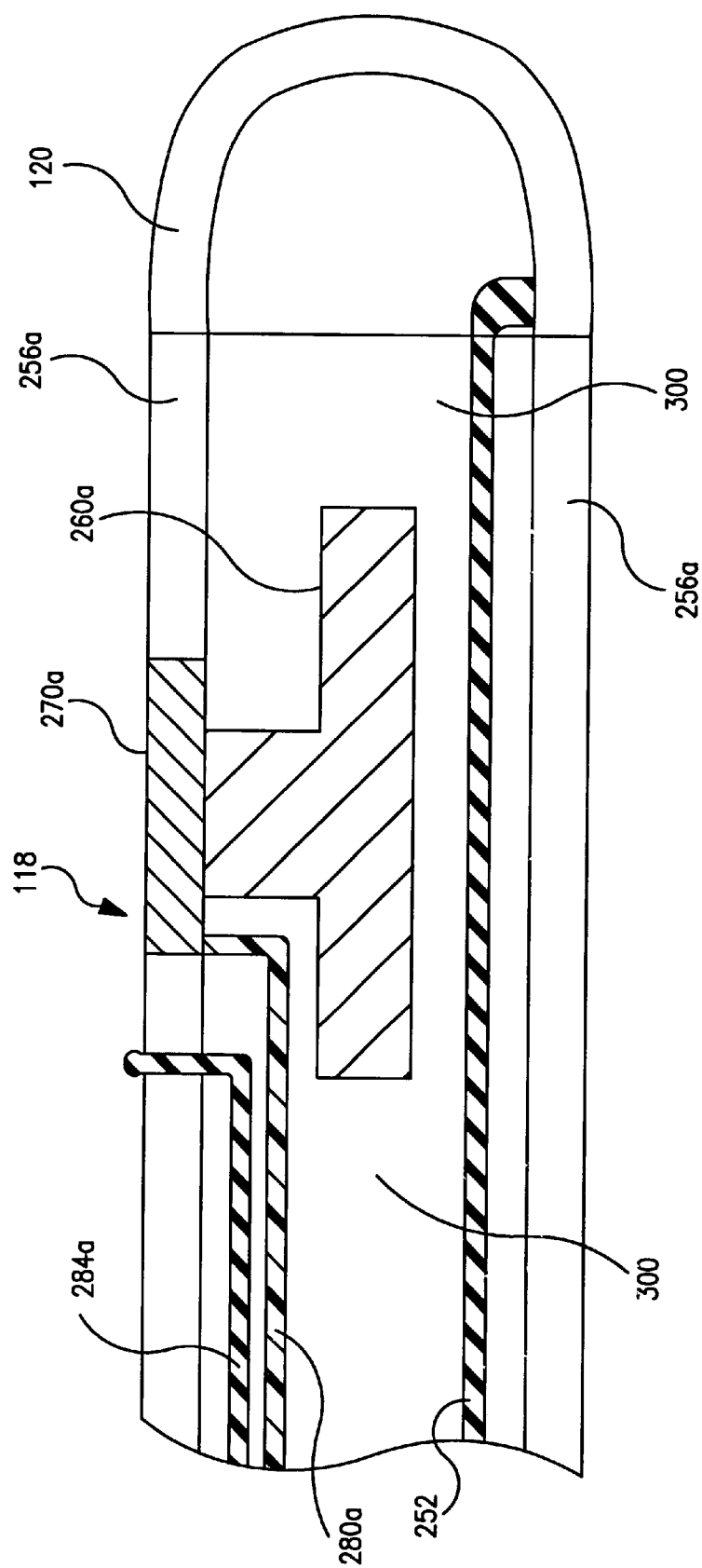
FIG. 8 is a side cutaway view of an alternative embodiment of the catheter assembly of FIG. 6.

FIG. 8 is a side cutaway view of an alternative embodiment of the inventive catheter assembly. In this embodiment, jacket 256a, which may be formed of PTFE or other bio-compatible material, surrounds an inner tubular member 300, which may be formed of silicone, for example. Tubular member is formed to define reservoir 260a, which is filled with a selected biologically-active agent. Reservoir 260a is capped by reservoir cap 270a formed in an etched or cutaway region of jacket 256a using any of the methods and materials discussed above. Reservoir cap 270a is coupled to anode conductor 280a, which is embedded within tubular member 300. Cathode conductor 284a is also embedded within tubular member, and extends through jacket 256a via an opening in the jacket as may be formed by etching, or cutting away, a portion of jacket 256a. Cathode conductor 284a is proximate to reservoir cap in a manner similar to that shown in FIG. 7 discussed above. In this embodiment, anode and cathode conductors 280a and 284a, respectively, may take the form of insulated wires. In one embodiment, these wires may comprise a twisted pair of wires.

FIG. 8 further shows conductor 252 embedded within tubular member 300 and coupled to electrode 120. In yet another embodiment, tubular member may include one or more inner lumens to carry one or more of the conductors. For example, a first lumen may be provided to carry conductor 252, and a second lumen may be provided to carry a twisted pair of conductors 280a and 284a.

As the number of reservoirs (and conductors) increases, the required number of mutually insulated conductors within the lead body correspondingly increases. Additional embodiments of the lead may include embedding multiple conductors within the wall of an insulative lead body, as disclosed in U.S. Pat. No. 5,968,087 issued to Hess, et al., U.S. Pat. No. 5,016,646 issued to Gotthardt, et al. and U.S. Pat. No. 5,845,396 issued to Altman et al. An additional alternative approach is disclosed in U.S. Pat. No. 5,935,159 issued to Cross et al, in which individual conductors are separated from one another by means of a central strut having laterally extending projections, serving to space and insulate adjacent conductors from one another, within a tubular outer sheath. Yet another approach is described below with respect to FIG. 16, and involves the use of a selection control circuit to selectably enable one or more of the multiple conductor pairs.

The foregoing embodiments of the inventive catheter assembly selectably release biologically-active agents by programmably causing the ionization of one or more conductive membranes. In another embodiment of the invention, the selectable release of biologically-active agents is triggered using a permanently cross-linked polymer gel of the type described in U.S. Pat. Nos. 5,651,979 and 5,876,741 incorporated herein by reference in their entireties. These polymer gels exhibit a reversible volume change when exposed to external environmental conditions. Of particular interest are known cross-linked polymer gels that swell to up to 300% of their volume when exposed to an electric field. Ones of these gels are biologically compatible, and are therefore suitable for use within implantable medical devices. For a more complete description of cross-linked polymer gels, see, for example, Tanaka Phys. Rev. Lett. 40(820), 1978; Tanaka et al., Phys. Rev. Lett. 38(771), 1977; Tanaka et al., Phys. Rev. Lett. 45(1636), 1980; llavsky, Macromolec. 15(782), 1982; Hrouz et al., Europ. Polym. J. 17, p361, 1981; Ohmine et al., J. Chem. Phys. 8(6379), 1984; Tanaka et al., Science 218(462), 1982; llavsky et al., Polymer Bull. 7(107), 1982; Gehrke "Responsive Gels:, Volume Transitions II", Dusek (ed.), Springer-Verlag, New York, p81–144, 1993; Liet al., Ann. Rev. Mat. Sci. 22(243), 1992; and Galaev et al., Enzyme Microb. Technol. 15(354), 1993.

Preferred responsive polymer gel network materials include polysaccharide chains cross-linked with a multifunctional carboxylic add obtainable from an acyl halide derivative of the acid. The preferred polymer chains are polysaccharides (e.g., starch or cellulose ethers) and the preferred multifunctional carboxylic acid is selected from the group consisting of adipic acid, sebacic acid, succinic acid, citric acid, 1, 2, 3, 4-butanetetracarboxylic acid, and 1, 10 decanedicarboxylic acid. Particularly preferred polymers are cellulose ethers selected from the group consisting of hydroxyethylcellulose, hydroxypropylcellulose, and hydroxypropylmethylcellulose. It is preferred that the gel exhibits substantially pressure independent volume changes at hydrostatic pressures in the range of 0.30–1.3 atmospheres. Methods of making cross-linked polymer networks are set forth in U.S. Pat. No. 5,651,979 references above.

Figure 9:
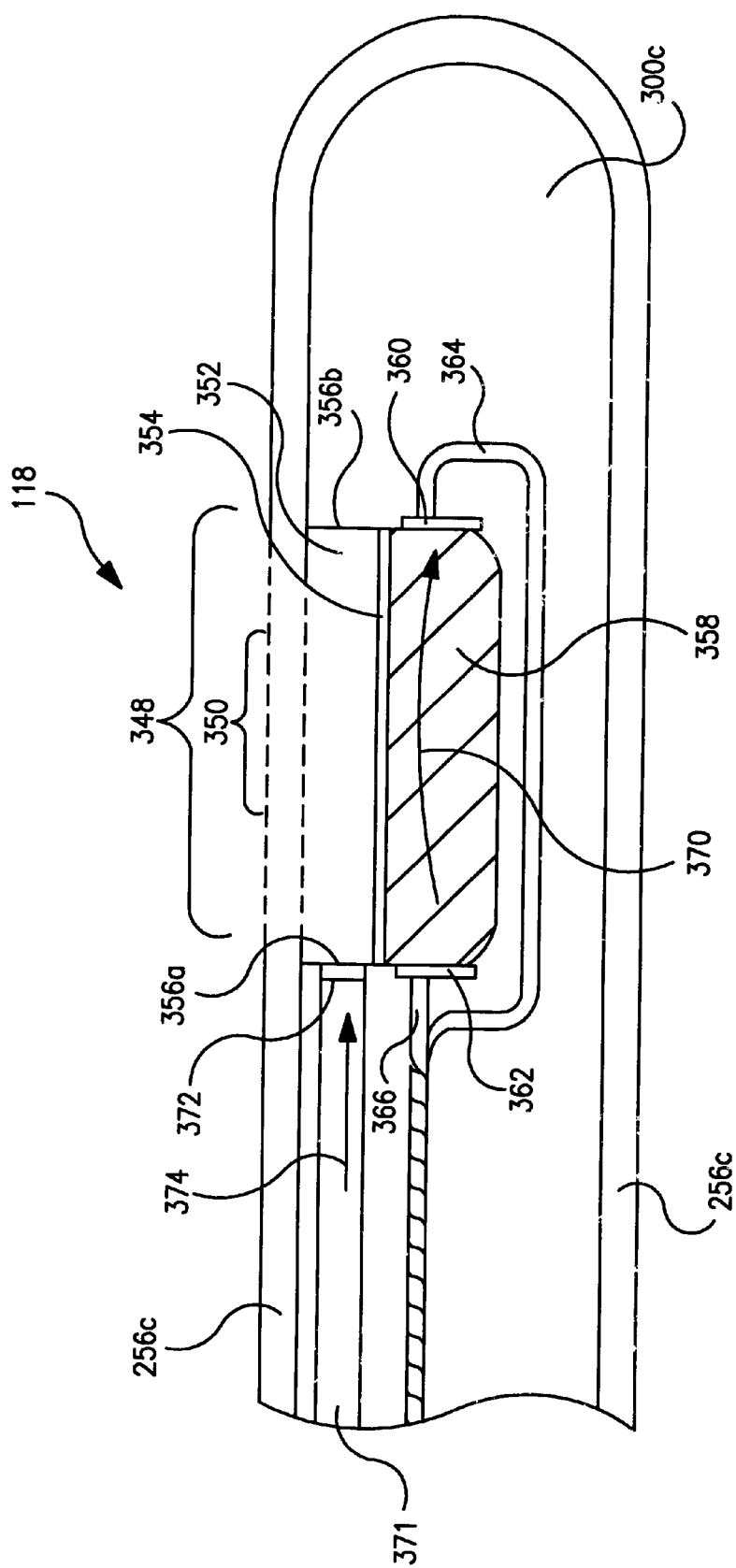
FIG. 9 is a side cutaway view of a catheter assembly that employs a cross-linked polymer gel to facilitate selectable delivery of biologically-active agents.

FIG. 9 is a side cutaway view of another embodiment of tip portion 118 of catheter assembly 2 which includes a cross-linked polymer gel of the type disclosed above to facilitate selectable delivery of biologically-active agents to a patient. Tip portion 118 includes an outer jacket 256c, which may be of any of the constructions discussed above. Jacket 256c surrounds a tubular member 300c that may be formed of silicone, for example. Jacket 256c includes a porous portion 348 containing one or more micropores 350 that are in fluid communication with reservoir 352. Porous portion of jacket 256c may be formed of a microporous structure such as porous Polytefrafluoroethylene (PTFE), which may be an expanded PTFE (e-PTFE). Alternatively, porous portion 348 may be created by puncturing jacket 256c at predetermined locations to create openings of a desired size and shape.

Porous portion 348 provides one or more sides of reservoir 352, which may contain any of the biologically-active agents discussed above, either in a pure gel, solid, or liquid form, or incorporated into a release system so that time-release of the agent may be possible. At least one wall of reservoir 352 is provided by a movable member 354, which in this embodiment slidably engages with walls 356a and 356b of reservoir 352. Movable member 354 is in communication with a second reservoir 358 that contains-one of the biologically-compatible cross-linked polymer gels discussed above that is responsive to electrical fields.

On at least two opposing sides of reservoir 358 is provided conductive members 360 and 362, each coupled to a respective one of conductors 364 and 366. Conductors 364 and 366 may be insulated wires as shown in FIG. 9. The conductive members may be embedded in tubular member 300c, or alternatively may-be carried by an internal lumen provided within tubular member 300c. A voltage potential applied between conductors 364 and 366 creates an electric field as indicated by arrow 370, causing the gel contained in reservoir 358 to swell. This, in turn, exerts a force against movable member 354, which pressurizes the biologically-active agent, dilating the pores 350 to release the biologically-active agent resident in reservoir 352. When a voltage difference between the conductor pairs 364 and 366 is no longer present, the gel resumes the original volume so that an agent resident in reservoir 352 is no longer forced through the micropores. It may be noted that in this embodiment, generation of the electric field across reservoir 358 involves little or no current drain, making this embodiment attractive for use in an implantable medical device.

In one embodiment of the invention, catheter assembly 102 includes a lumen 371 in fluid communication with remote storage reservoir 213 coupled to infusion pump 209 of FIG. 5.

In an embodiment including a pump, a liquid biologically-active agent may be pumped into reservoir 352 via a one-way valve 372, as indicated by arrow 374. Pressure created in lumen 370 by the activation of the pump opens the one-way value 372 to infuse an agent into reservoir 352. One-way valve then closes when the pump is de-activated. This provides a mechanism to re-fill reservoir 352 with an additional amount of a selected agent. In a preferred embodiment, pump is activated when gel in reservoir 358 is in the unexpanded state. A sensor may be provided in communication with reservoir 352 to indicate when the reservoir is empty.

Figure 10:
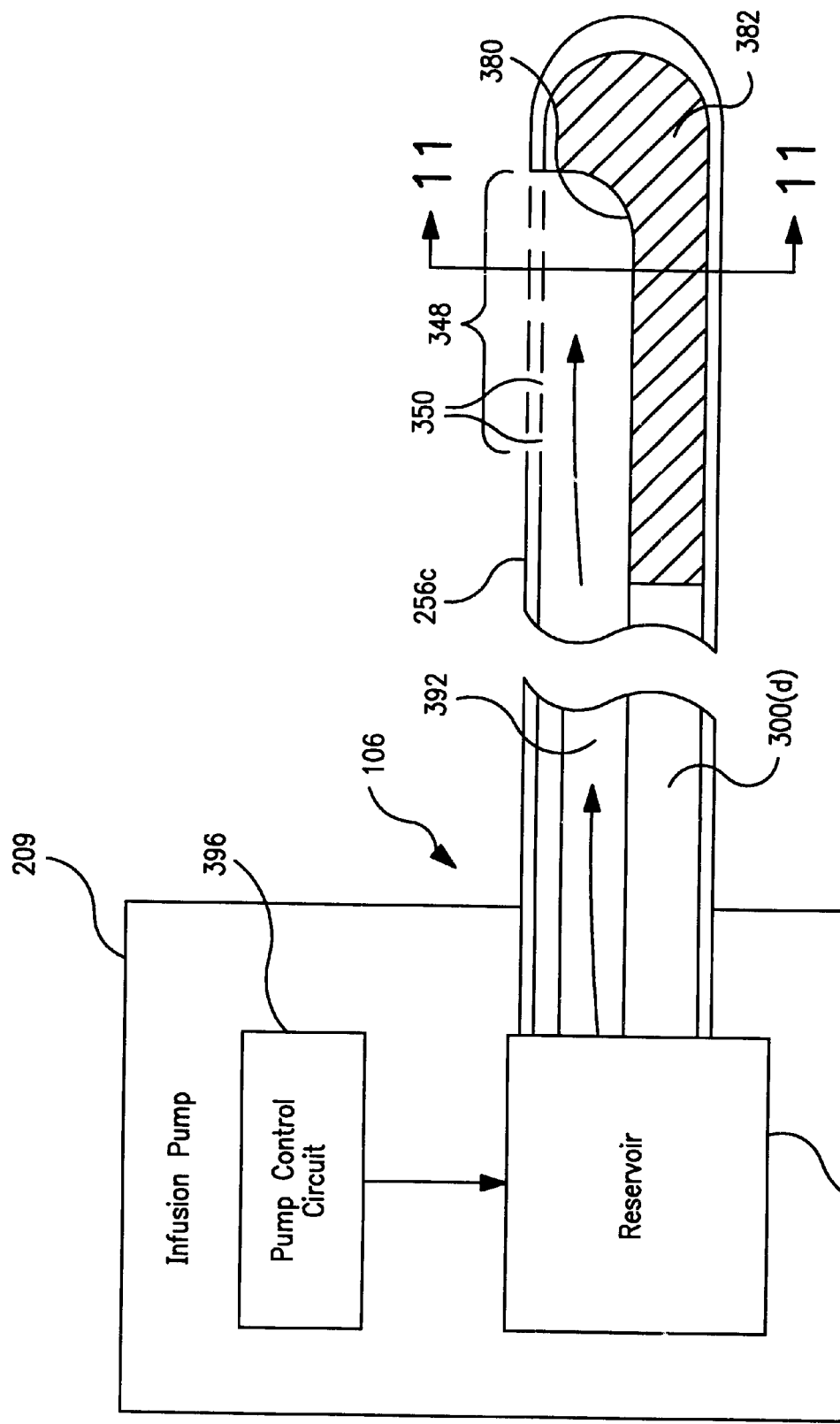
FIG. 10 is a side cutaway view of another embodiment of the catheter wherein a cross-linked polymer gel in the expanded state is employed to prevent a biologically-active agent from exiting a catheter port.

FIG. 10 is a side cutaway view of another embodiment of the inventive system that includes a cross-linked polymer gel to facilitate selectable drug delivery. In this embodiment, jacket 256c defines an inner space that includes a flexible member 380. Flexible member may extend within tip portion 118, and may further extend within all, or a portion of, body portion 116. Flexible member defines one or more walls of reservoir 382, which is filled with a cross-linked polymer gel. In this embodiment, catheter assembly further includes a lumen 392 extending from porous portion 348 to the proximal assembly 106, which is coupled to infusion pump 209 (FIG. 5). Pump assembly includes a pump control circuit 396 coupled to reservoir 213. This pump may operate as described in U.S. Pat. 5,820,589 referenced above.

In the embodiment of FIG. 10, drug delivery is accomplished when the gel in an unexpanded state within reservoir 213. Infusion pump 209 is activated to deliver biologically-active agent within reservoir 213 to lumen 392. Pressure created within lumen 392 by operation of the pump forces the agent from pores 350. To disable the delivery of the agent, the pump is turned off, and an electric field is created across reservoir 382. This causes the cross-linked polymer gel in reservoir 382 to expand, forcing the flexible member 380 to collapse against porous portion 348 so that delivery of an agent within lumen 392 is interrupted.

Figure 11:
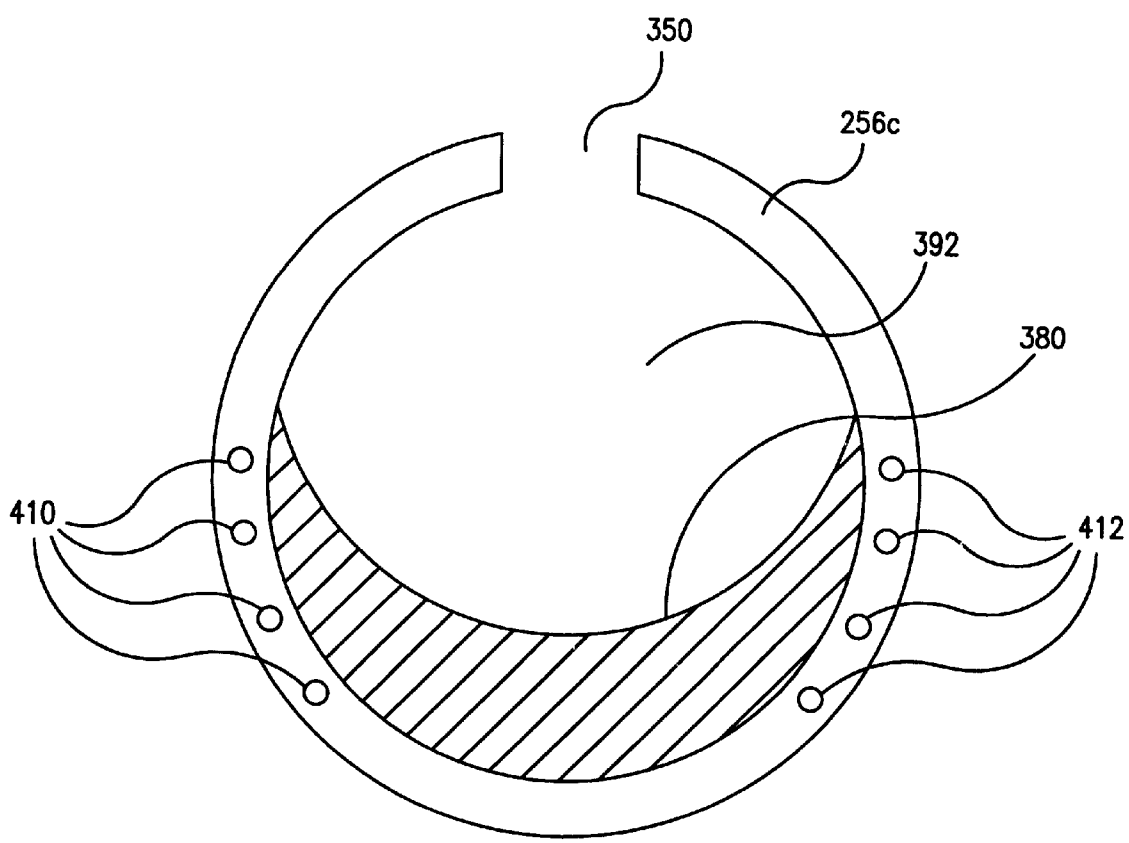
FIG. 11 is a cross-sectional view of the catheter assembly of FIG. 10 illustrating the polymer gel in a non-expanded state.

FIG. 11 is a cross-sectional view of the catheter assembly of FIG. 10 at line 11—11 illustrating operation of the system when the polymer gel is in a non-expanded state. Lumen 392, which is partially defined by flexible member 380, is open to allow the flow of biologically-active agents to pores 350 under pressure developed by the infusion pump 209. This view shows conductors 410 and 412 embedded within jacket 256c. These conductors extend to a control circuit such as shown in FIG. 5 located in IMD 2. For example, all of conductors 410 may be electrically coupled to one another, and to one of the conductors included in a conductor pair of FIG. 5. Likewise, conductors 412 may all be electrically coupled to one another, and to the other conductor in the same conductor pair. Thus, by selectively activating a predetermined one of the conductor pairs shown as 218, 220, and 222 of FIG. 5, the electrical field may be generated across the polymer gel, as discussed below.

Figure 12:
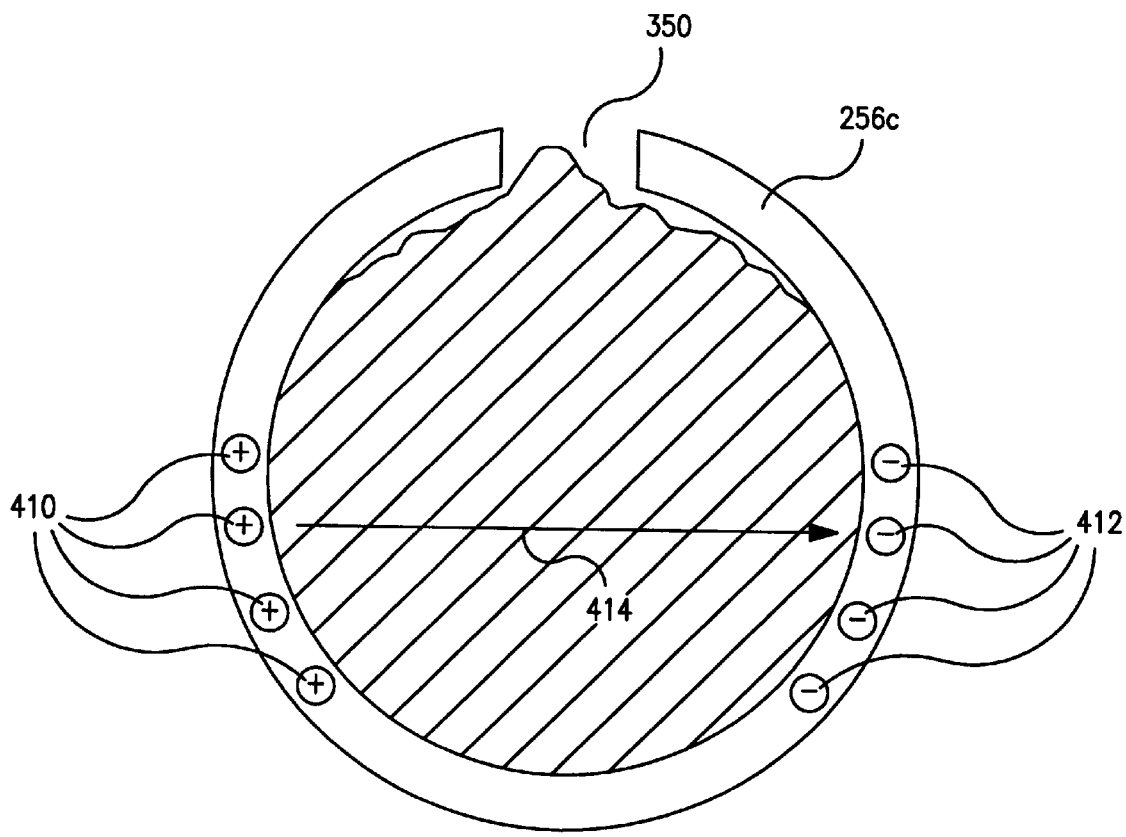
FIG. 12 is a cross-sectional view of the catheter assembly of FIG. 10 illustrating the polymer gel in an expanded state.

FIG. 12 is a cross-sectional view of the catheter assembly of FIG. 10 at line 11—11 illustrating operation of the system when the polymer gel is in an expanded state. The polymer gel expands in response to the electric field created by a voltage potential difference existing between conductors 410 and 412, as shown by arrow 414. This forces flexible member 380 to collapse against pores 350, interrupting the delivery of an agent present within lumen 392. In the preferred embodiment, when the electric field is generated, infusion pump 209 is turned off.

As noted above, the inventive catheter system may be used in any application wherein the controlled delivery of biologically-active agents to a body is desirable. In one embodiment, multiple ones of the inventive catheters may be used to deliver biologically-active agents to predetermined nerves in a patient's body to control the rate of a patient's heart.

FIG. 13 is a top view of yet another embodiment of a catheter for use in selectably delivering biologically-active agents using polymer gels. FIG. 13 illustrates tip portion 118 of the catheter assembly, including an electrode 120. Catheter includes one or more apertures such as aperture 420. Aligned with aperture and embedded within the wall of the catheter is a disk member 422 (shown dashed). The disk is defined by a flexible, expandable material which is shaped like "donut". The disk is filled with a polymer gel that expands when placed in an electrical field, as discussed above. A pair of conductors 424 and 426 (shown dashed) are also embedded within the wall of the catheter, and are positioned so that an electrical field may be generated across disk 422 to control expansion of the polymer gel contained by the disk. This expansion thereby prevents the biologically-active agent from exiting the catheter via aperture 420. Because the embodiment of FIG. 13 provides a mechanism to close the aperture 420, this embodiment has the advantage of prevent the ingress of body fluids into the catheter. For example, the closure of the disk aperture prevents the ingress of blood which could subsequently form clots, preventing further use of aperture 420.

FIG. 14A is a top plan view of disk 422 when the polymer gel contained by the disk is not located within an electrical field. Because the polymer gel is not in the electrical field, the gel contracts, allowing aperture 430 to open and provide a passage for the delivery of a drug bolus.

FIG. 14B is a top plan view of disk 422 when the polymer gel contained by the disk is located within an electrical field, causing the gel to expand so that aperture 430 is closed.

FIG. 14C is a side plan view of disk 422 when the disk is in either the expanded or contracted state. It may be noted that to prevent the overall size of the disk from expanding when the polymer gel expands, the outer walls of the disk may be made of a material that is more rigid than the inner walls of the disk that surround the aperture. Both the inner and outer walls may be made of a material such as rubber selected to have a desired stiffness, for example.

Figure 15:
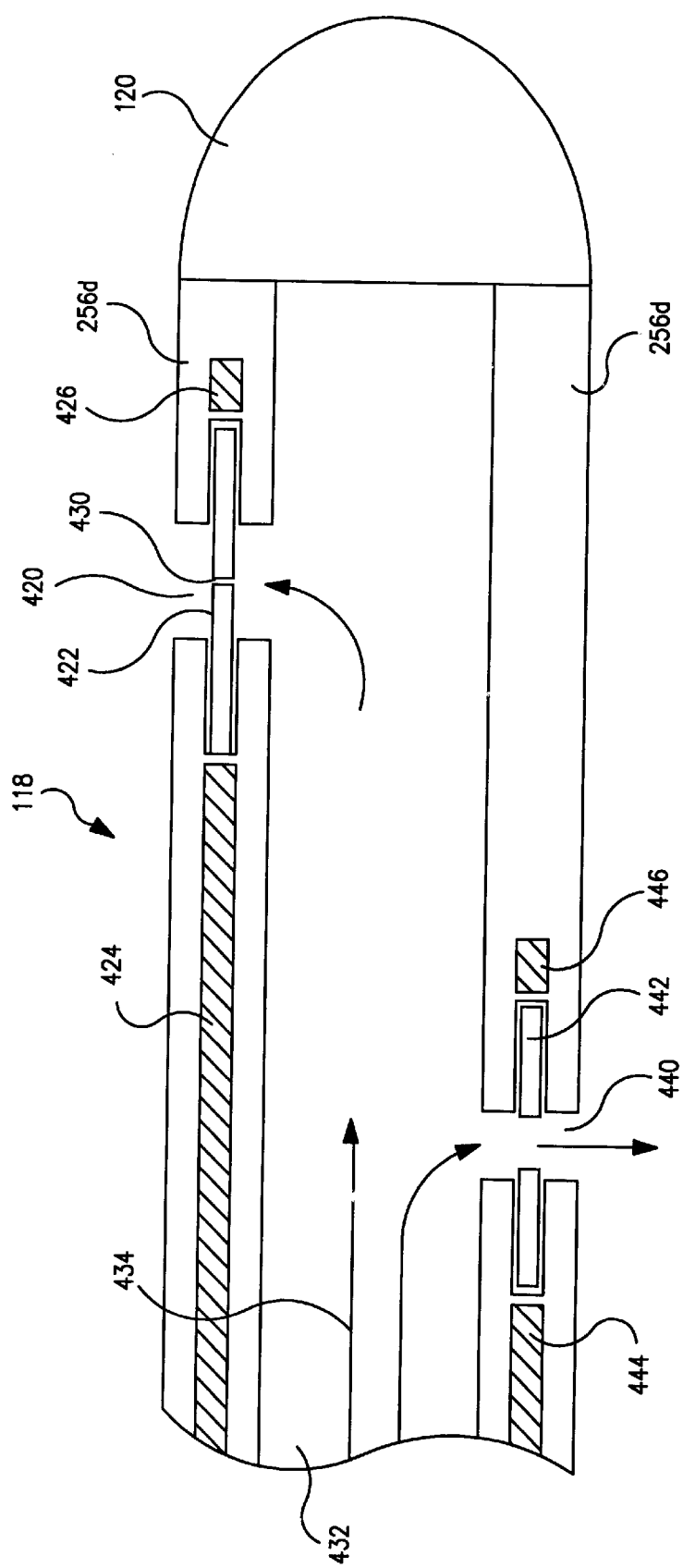
FIG. 15 is a side cutaway view of the embodiment of the catheter of FIG. 13 along line 15—15.

FIG. 15 is a side cutaway view of the embodiment of catheter of FIG. 13 along line 15—15. This view illustrates jacket 256d, which may be formed of a polymer or silicon, forming the walls of catheter in the manner discussed above. This view further illustrates inner lumen 432 that is in fluid communication with a reservoir (FIG. 5) for storing biologically-active agents. When an infusion pump is activated, the biologically-active agents are pumped into lumen in the manner shown by arrow 434.

FIG. 15 illustrates the manner in which disk 422 is embedded within the wall of the catheter. In this view, disk 422 is in an expanded state so that aperture 430 is closed. As discussed above, the expansion is causes by the generation of an electrical field between conductors 424 and 426. When in the expanded state, disk 422 prevents the biologically-active agents contained in inner lumen 432 from exiting catheter lumen 420.

The catheter of the present embodiment may include multiple apertures within the catheter wall in tip portion 118, and/or in the body portion 116, of the catheter assembly. As with any of the embodiments described above, these apertures may be staggered around the circumference of the catheter to ensure that one of the apertures is always available to perform drug delivery regardless of the manner in which the catheter is positioned within the body. For example, in some instances, one or more of the apertures may be blocked because of close contact with body tissue. By providing multiple apertures at various staggered locations around the body of the catheter, it is more likely one of the apertures will not be blocked, and will be available to deliver the biologically-active agents. For example, FIG. 15 illustrates a second aperture 440 aligned with disk 442. Disk 442 is in an unexpanded state because no electrical field is being generated between conductors 444 and 446. As such, the material within lumen 432, which is under pressure because of the operation of infusion pump 209, is allowed to exit aperture 440.

In any of the embodiments of the drug infusion catheter discussed above, the pores or apertures through which the drugs are delivered may be a varying sizes. By selectably controlling drug delivery through one or more apertures of differing sizes, a precise, selectable quantity of a drug may be delivered to the body. In one embodiment, a catheter may include multiple apertures, wherein ones of the apertures have a cross-sectional area that is twice the size of a respective other one of the apertures. In this manner, the apertures may comprise a binary-sized array. A control circuit may be provided in IMD 2 that is similar to decode circuit 216 that allows a predetermined combination of apertures to be activated to deliver a precise dosage of a biologically-active agent to a patient's body.

Figure 16:
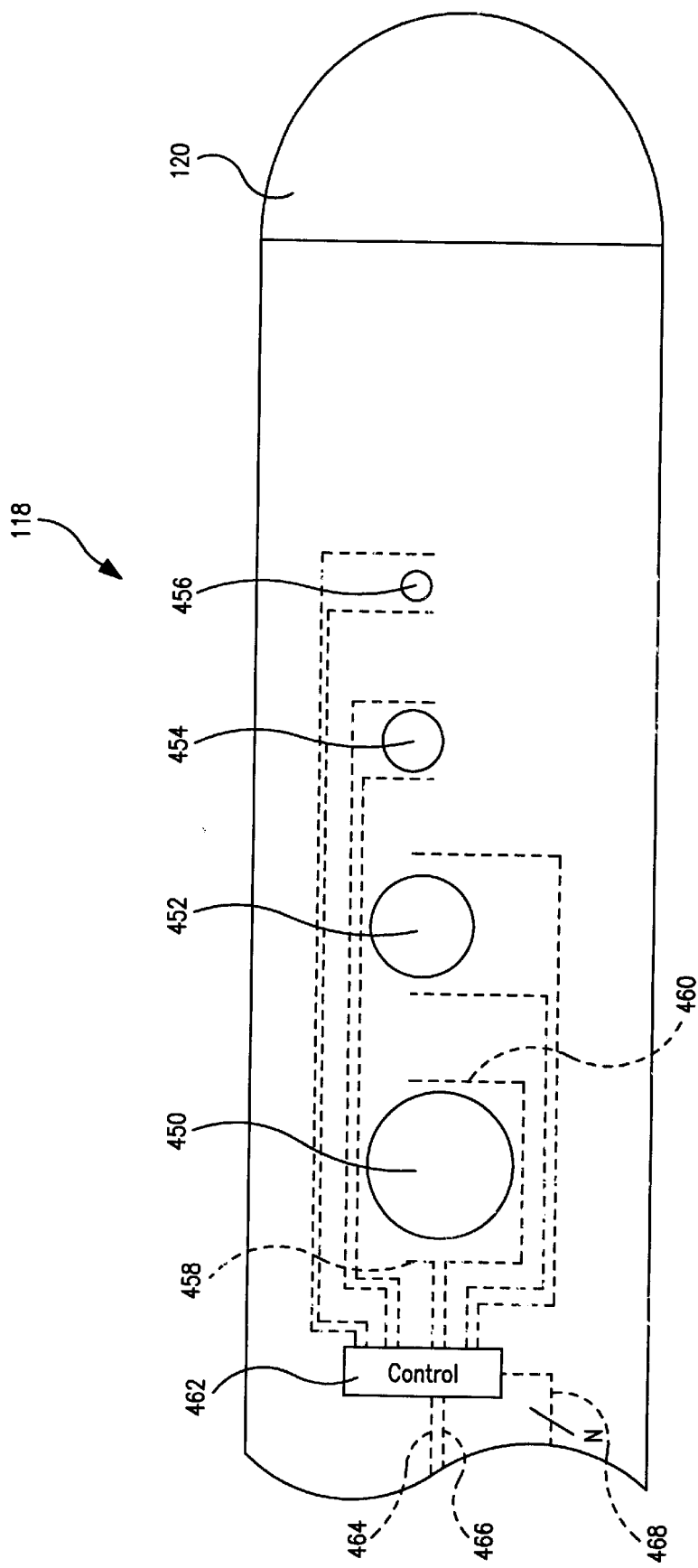
FIG. 16 is a top plan view of a distal portion of a catheter body including a binary array of apertures.

FIG. 16 is a top plan view of a distal portion of a catheter body including a binary array of apertures. Each of the apertures may be controlled in a manner similar to that described with respect to the disk members of FIGS. 13 and 15, or using any of the other control mechanisms discussed above. Although only four apertures are shown in FIG. 16, it is understood fewer, or more, than the number of apertures shown may be used in this embodiment. Aperture 450 has a cross-sectional area that is twice as large as aperture 452, which has a cross-sectional area that is twice as large as aperture 454, which, in turn, has a cross-sectional area that is twice as large as aperture 456. Although this type of array is shown for use with a catheter that utilizes a cross-linked polymer gel, it is understood this type of array could be included in any of the embodiments of the current invention, including those embodiments that utilize a dissolvable conductive cap member to selectively accomplish drug delivery. U.S. Pat. No. 5,368,704 entitled "Micro-electrochemical Valves and Method" discloses a binary valve configuration for controlling flow in a precise manner such as controlled by the aperture array of the embodiment shown in FIG. 16.

In the embodiment illustrated in FIG. 16, each of the apertures is associated with a respective pair of conductors (shown dashed) to provide individual control of the flow through the associated aperture. For example, the regulation of the flow through aperture 450 is controlled by conductors 458 and 460 in a manner similar to that discussed above with respect to FIG. 15. Each of the conductor pairs may extend to the proximal end of the catheter assembly in the manner described above. However, as the number of conductor pairs increases, an alternative conductor configuration as shown in FIG. 16 may be more desirable. According to this aspect of the invention, a control circuit 462 may be included at a location within main body portion II 6 or tip portion 118 of the catheter assembly. A single pair of conductors 464 and 466 extends from control circuit 462 to the proximal end of the catheter assembly, and may be driven by a circuit in IMD 2. That is, a voltage potential difference is provided on lines 464 and 466 to control circuit 462. The control circuit then transfers the potential difference to one or more of the conductor pairs at its output as determined by a set of control lines 468 which may also be driven by IMD 2. In one embodiment, control circuit 462 is a multiplexer for driving a predetermined one of the conductor pairs at a time. In this embodiment, the multiplexer may be controlled to sequentially enable predetermined ones of the conductor pairs, and to thereby deliver the desired drug dosage to a patient. In another embodiment, control circuit may be a combinational logic circuit capable of enabling predetermined multiple ones of the conductor pairs in parallel. In either case, the use of the control circuit eliminates the need to have all of the conductors in the conductor pairs extend to the proximal end of the catheter assembly. The catheter assembly may therefore be reduced in size. This type of control circuit may be readily incorporated into any of the embodiments of the invention described herein.

Although for ease of illustrate, the embodiment of FIG. 16 depicts the apertures substantially aligned, it may be preferable to stagger the apertures around the circumference of the catheter. This arrangement minimizes the generation of unintentional electric fields in the vicinity of one or more of the apertures as a result of the existence of potential differences generated in conductor pairs associated with other ones of the apertures.

Although use of the present invention has been described with reference to preferred embodiments, workers skilled in the art will recognize that changes can be made in form and detail without departing from the spirit and scope of the invention. For example, the current drug delivery system may further include any of the aspects of the system described in commonly-assigned U.S. Pat. No. 6,178,349 issued Jan. 23, 2001 entitled "Drug Delivery Neural Stimulation Device for Treatment of Cardiovascular Disorders" incorporated herein by reference in its entirety.

What is claimed is:

1. A device to provide the controlled release of a biologically-active agent contained therein to a body, comprising:
   a cap member, formed of a conductive material, preventing the agent from passing outward from the device to the body;
   a first conductor electrically and mechanically coupled to the cap member; and
   a second conductor electrically and mechanically isolated from the cap member, the first conductor and the second conductor forming a circuit when a voltage potential difference is generated between the first conductor and the second conductor, the voltage potential difference causing ionization of the cap member to enable the biologically-active agent to pass outward from the device to the body.

2. The device of claim 1, wherein the conductive material forming the cap member is one of copper, gold, silver and zinc.

3. The device of claim 1, wherein the conductive material forming the cap member is a polymer material.

4. The device of claim 1, further comprising a control circuit coupled to the device to selectably generate the voltage potential difference between the first conductor and the second conductor.

5. The device of claim 4, further comprising at least one electrode carried by the device to provide electrical stimulation to the body.

6. The device of claim 5, wherein the control circuit includes processing means for coordinating the delivery of the biologically-active agent with the electrical stimulation.

7. The device of claim 6, wherein the electrode is adapted to provide cardioversion/defibrillation stimulation, and wherein the processing means controls the delivery of the biologically-active agent prior to delivery of the cardioversion/defibrillafion stimulation to reduce patient discomfort associated with the cardioversion/defibrillation stimulation.

8. The device of claim 1, further comprising at least one biological sensor carried by the device to provide a signal indicative of a physiological condition.

9. The device of claim 8, wherein the control circuit includes processing means to control the delivery of the biologically-active agent in response to the signal indicative of the physiological condition.

10. A device to provide the controlled release of a biologically-active agent to a body, comprising:
   an outer portion extending from a proximal assembly to a tip portion of the device and defining a plurality of ports through which the biologically-active agent is released from the device to the body;
   a plurality of reservoirs containing the biologically-active agent, the plurality of reservoirs formed along the outer portion in fluid communication with the plurality of ports;
   a plurality of cap members, formed of a conductive material, positioned over the plurality of reservoirs and preventing the agent from passing outward to the body from the plurality of reservoirs through the plurality of ports;

a plurality of conductor pairs, each of the plurality of conductor pairs including a first conductor, extending from the proximal assembly to the tip portion and electrically and mechanically coupled to one reservoir of the plurality of reservoirs, and a second conductor extending from the proximal assembly to the tip portion and electrically and mechanically isolated from the one reservoir, the first conductor and the second conductor forming a circuit when a voltage potential difference is generated between the first conductor and the second conductor, the voltage potential difference causing ionization of a corresponding one of the plurality of cap members to enable the biologically-active agent to flow from the one reservoir to the body through a corresponding port of the plurality of ports.

11. The device of claim 10, wherein the conductive material forming the plurality of cap members is one of copper, gold, silver and zinc.

12. The device of claim 10, wherein the plurality of cap members are formed of a polymer material.

13. The device of claim 10, further comprising a control circuit coupled to the device to selectably generate the voltage potential difference between the first conductor and the second conductor.

14. The device of claim 13, further comprising at least one electrode carried by the device to provide electrical stimulation to the body.

15. The device of claim 14, wherein the control circuit includes processing means for coordinating the delivery of the biologically-active agent with the electrical stimulation.

16. The device of claim 15, wherein the electrode is adapted to provide cardioversion/defibrillation stimulation, and wherein the processing means controls the delivery of the biologically-active agent prior to delivery of the cardioversion/defibrillation stimulation to reduce patient discomfort associated with the cardioversion/defibrillation stimulation.

17. The device of claim 16, further comprising at least one biological sensor carried by the device to provide a signal indicative of a physiological condition.

18. The device of claim 17, wherein the control circuit includes processing means to control the delivery of the biologically-active agent in response to the signal indicative of the physiological condition.

19. The device of claim 10, wherein the plurality of reservoirs include a first reservoir and a second reservoir, and the biologically-active agent corresponds to a first compound within the first reservoir and to a second compound, different from the first compound within the second reservoir.

20. A method of delivering a biologically-active agent to a body, comprising the steps of:

positioning a device providing the controlled release of the biologically-active along a predetermined location within the body, the device having at least one cap member, formed of a conductive material, preventing the agent from passing outward from the device to the body; and generating a voltage potential difference between a first conductor electrically and mechanically coupled to the cap member, and a second conductor electrically and mechanically isolated from the cap member, the voltage potential difference causing ionization of the cap member to enable the biologically-active agent to pass outward from the device to the body.

* * * * *

(12) EX PARTE REEXAMINATION CERTIFICATE (6036th)
United States Patent
Thompson

(10) Number: US 6,571,125 C1
(45) Certificate Issued: Dec. 4, 2007

(54) DRUG DELIVERY DEVICE

(75) Inventor: David L. Thompson, Andover, MN (US)

(73) Assignee: Medtronic, Inc., Minneapolis, MN (US)

Reexamination Request:
No. 90/007,741, Sep. 30, 2005

Reexamination Certificate for:
| | |
|---|---|
| Patent No.: | 6,571,125 |
| Issued: | May 27, 2003 |
| Appl. No.: | 09/781,750 |
| Filed: | Feb. 12, 2001 |

(51) Int. Cl.
*A61M 5/142* (2006.01)
*A61M 5/168* (2006.01)

(52) U.S. Cl. .................................. 604/20; 604/891.1
(58) Field of Classification Search .................. None
See application file for complete search history.

(56) References Cited

U.S. PATENT DOCUMENTS

| | | | | |
|---|---|---|---|---|
| 5,041,107 | A | * 8/1991 | Heil, Jr. ................ | 604/891.1 |
| 5,662,689 | A | * 9/1997 | Elsberry et al. ............. | 607/5 |
| 5,797,898 | A | 8/1998 | Santini, Jr. et al. | |
| 6,123,861 | A | 9/2000 | Santini, Jr. et al. | |
| 6,178,349 | B1 | * 1/2001 | Kieval ........................ | 607/3 |
| 6,491,666 | B1 | 12/2002 | Santini, Jr. et al. | |

* cited by examiner

Primary Examiner—Peter C. English

(57) ABSTRACT

An Implantable Medical Device (IMD) for controllably releasing a biologically-active agent such as a drug to a body is disclosed. The IMD includes a catheter having one or more ports, each of which is individually controlled by a respective pair of conductive members located in proximity to the port. According to the invention, a voltage potential difference generated across a respective pair of conductive members is used to control drug delivery via the respective port. In one embodiment of the current invention, each port includes a cap member formed of a conductive material. This cap member is electrically coupled to one of the conductive members associated with the port to form an anode. The second one of the conductive members is located in proximity to the port and serves as a cathode. When the cap member is exposed to a conductive fluid such as blood, a potential difference generated between the conductors causes current to flow from the anode to the catheter, dissolving the cap so that a biologically active agent is released to the body. In another embodiment of the invention, each port is in proximity to a reservoir or other expandable member containing a cross-linked polymer gel of the type that expands when placed within an electrical field. Creation of an electric field between respective conductive members across the cross-linked polymer gel causes the gel to expand. In one embodiment, this expansion causes the expandable member to assume a state that blocks the exit of the drug from the respective port. Alternatively, the expansion may be utilized to assert a force on a bolus of the drug so that it is delivered via the respective port. Drug delivery is controlled by a control circuit that selectively activates one or more of the predetermined ports.

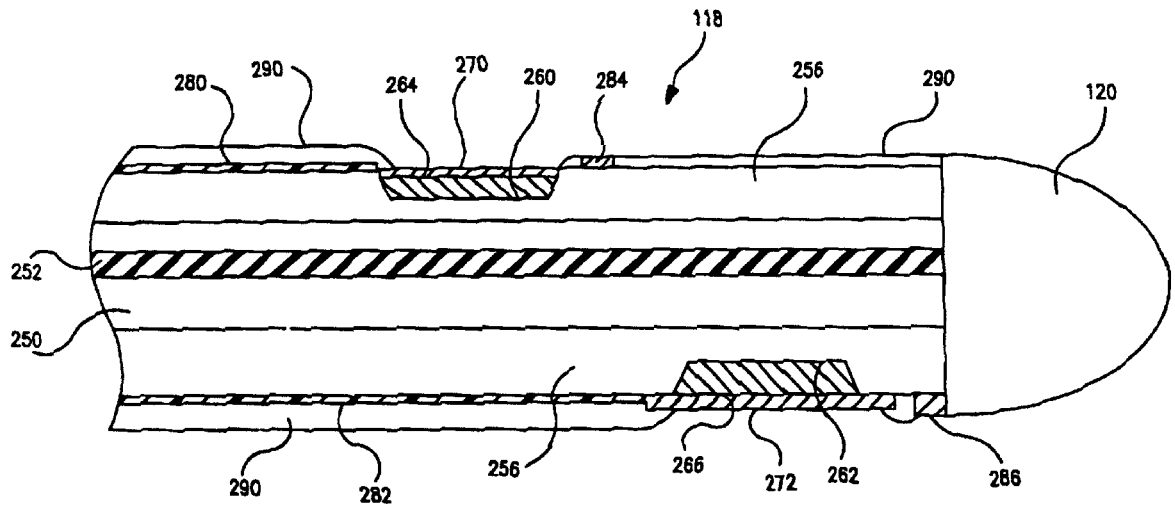

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 10 and 20 are determined to be patentable as amended.

Claims 2–9 and 11–19, dependent on an amended claim, are determined to be patentable.

1. A device to provide the controlled release of a biologically-active agent contained therein to a body, comprising:
   *a catheter including a main body portion and a tip portion, the catheter having a port in the tip portion through which the biologically-active agent is released from the device to the body;*
   a cap member, formed of a conductive material, [preventing] *closing the port to prevent* the agent from passing outward [from the device] *through the port* to the body;
   a first conductor electrically and mechanically coupled to the cap member; and
   a second conductor electrically and mechanically isolated from the cap member, the first conductor and the second conductor forming a circuit when a voltage potential difference is generated between the first conductor and the second conductor, the voltage potential difference causing ionization of the cap member to enable the biologically-active agent to pass outward from the device to the body.

10. A device to provide the controlled release of a biologically-active agent to a body, comprising:
    [an outer] *a catheter including a main body* portion extending from a proximal assembly to a tip portion of the device and defining a plurality of ports *in the tip portion through which the biologically-active agent is released from the device to the body;*
    a plurality of reservoirs containing the biologically-active agent, the plurality of reservoirs formed along the [outer] *tip* portion in fluid communication with the plurality of ports;
    a plurality of cap members, formed of a conductive material, positioned over the plurality of reservoirs and [preventing] *closing the ports to prevent* the agent from passing outward to the body from the plurality of reservoirs through the plurality of ports;
    a plurality of conductors pairs, each of the plurality of conductor pairs including a first conductor, extending from the proximal assembly to the tip portion and electrically and mechanically coupled to one reservoir of the plurality of reservoirs, and a second conductor extending from the proximal assembly to the tip portion and electrically and mechanically isolated from the one reservoir, the first conductor and the second conductor forming a circuit when a voltage potential difference is generated between the first conductor and the second conductor, the voltage potential difference causing ionization of a corresponding one of the plurality of cap members to enable the biologically-active agent to flow from the one reservoir to the body through a corresponding port of the plurality of ports.

20. A method of delivering a biologically-active agent to a body, comprising the steps of:
    positioning a [device] *catheter including a main body portion and a tip portion within the body so that a port in the tip portion is positioned for* providing the controlled release of the biologically-active [along] *agent at* a predetermined location within the body, the [device] *catheter* having at least one cap member, formed of a conductive material, [preventing] *closing the port to prevent* the agent from passing outward [from the device] *through the port* to the body; and
    generating a voltage potential difference between a first conductor electrically and mechanically coupled to the cap member, and a second conductor electrically and mechanically isolated from the cap member, the voltage potential difference causing ionization of the cap member to enable the biologically-active agent to pass outward from the [device] *port* to the body.

* * * * *